United States Patent
Crabb et al.

(10) Patent No.: US 9,861,276 B2
(45) Date of Patent: Jan. 9, 2018

(54) SUPRA-THRESHOLD TEST AND A SUB-PIXEL STRATEGY FOR USE IN MEASUREMENTS ACROSS THE FIELD OF VISION

(75) Inventors: David Crabb, London (GB); Ciara Bergin, London (GB); David Garway-Heath, London (GB); Gay Verdon-Roe, London (GB); Mark Westcott, London (GB)

(73) Assignee: UCL BUSINESS PLC, London (GB)

( * ) Notice: Subject to any disclaimer, the term of this patent is extended or adjusted under 35 U.S.C. 154(b) by 351 days.

(21) Appl. No.: 13/696,058

(22) PCT Filed: May 5, 2011

(86) PCT No.: PCT/GB2011/000689
§ 371 (c)(1),
(2), (4) Date: Mar. 27, 2013

(87) PCT Pub. No.: WO2011/138587
PCT Pub. Date: Nov. 10, 2011

(65) Prior Publication Data
US 2013/0201452 A1      Aug. 8, 2013

Related U.S. Application Data

(60) Provisional application No. 61/332,023, filed on May 6, 2010.

(30) Foreign Application Priority Data

May 7, 2010   (GB) .................................. 1007697.4

(51) Int. Cl.
    *A61B 3/024*      (2006.01)
(52) U.S. Cl.
    CPC .................................. *A61B 3/024* (2013.01)

(58) Field of Classification Search
    CPC ....................................................... A61B 3/024
    (Continued)

(56) References Cited

U.S. PATENT DOCUMENTS 3,664,732 A  *  5/1972  Lynn ...................... A61B 3/024
                                                    351/224
3,883,234 A     5/1975  Lynn et al.
(Continued)

FOREIGN PATENT DOCUMENTS

CN         86108966 A       7/1987
CN        101336823 A       1/2009
(Continued)

OTHER PUBLICATIONS

Garway-Heath, D. F., J. Caprioli, et al. Scaling the hill of vision: the physiological relationship between light sensitivity and ganglion cell numbers. Invest Ophthalmol Vis Sci. 2000a. 41 (7): 1774-82.
(Continued)

*Primary Examiner* — Zachary Wilkes
(74) *Attorney, Agent, or Firm* — Park, Vaughan, Fleming & Dowler LLP

(57) ABSTRACT

One embodiment of the invention provides a method for performing a supra-threshold test of sensitivity across a visual field of a subject. The method includes presenting a stimulus at each location of a set of locations spread across the visual field and obtaining for each stimulus a result indicating whether or not the stimulus was seen by the subject. The method further includes determining for each location whether or not to re-present a stimulus at that location, wherein for a given location, the determining involves combining results obtained from multiple locations. These multiple locations are defined by a cluster
(Continued)

associated with the given location, with the cluster being determined based on the paths of optic nerve fibre bundles across the visual field.

14 Claims, 14 Drawing Sheets

(58) Field of Classification Search
USPC .................................................. 351/224
See application file for complete search history.

(56) References Cited

U.S. PATENT DOCUMENTS

| | | | |
|---|---|---|---|
| 3,883,235 A * | 5/1975 | Lynn | A61B 3/024 |
| | | | 351/224 |
| 4,334,738 A | 6/1982 | Seekinger | |
| 5,050,983 A | 9/1991 | Johnson et al. | |
| 5,187,507 A | 2/1993 | Arden | |
| 5,341,153 A | 8/1994 | Benzschawel et al. | |
| 5,461,435 A | 10/1995 | Rootzen et al. | |
| 5,864,385 A * | 1/1999 | Gonzales de la Rosa | |
| | | | A61B 3/024 |
| | | | 351/224 |
| 5,912,723 A | 6/1999 | Maddess | |
| 6,045,515 A | 4/2000 | Lawton | |
| 6,527,391 B1 * | 3/2003 | Heiji | A61B 3/024 |
| | | | 351/243 |
| 2002/0109819 A1 | 8/2002 | Tuval | |
| 2004/0057013 A1 | 3/2004 | Cappo et al. | |
| 2009/0180071 A1 | 7/2009 | Fateh | |
| 2009/0180074 A1 | 7/2009 | Fateh | |
| 2013/0201452 A1 | 8/2013 | Crabb et al. | |

FOREIGN PATENT DOCUMENTS

| | | |
|---|---|---|
| CN | 201384484 Y | 4/2009 |
| DE | 19627848 A1 | 7/1996 |
| EP | 206069 | 7/1982 |
| EP | 0911762 A3 | 4/1999 |
| EP | 2014222 A1 | 6/2008 |
| EP | 2566379 B1 | 11/2016 |
| JP | 2002172089 | 12/2000 |
| JP | 2003093344 | 9/2001 |
| JP | 2007319408 | 5/2006 |
| WO | 9816150 A1 | 4/1998 |
| WO | 0040140 A1 | 7/2000 |
| WO | 0230291 A1 | 4/2002 |
| WO | 03065964 A1 | 8/2003 |
| WO | 2004093668 A1 | 11/2004 |
| WO | 2007109724 A1 | 9/2007 |
| WO | 2007113484 A1 | 10/2007 |
| WO | 2008005848 A3 | 10/2008 |
| WO | 2009059380 A1 | 5/2009 |
| WO | 2011138587 A8 | 11/2011 |

OTHER PUBLICATIONS

Garway-Heath, D. F., Poinoosawmy D, Fitzke FW. Hitchings RA. Mapping the visual field to the optic disc in normal tension glaucoma eyes. Ophthalmology. 2000b;107(10):1809-15.

Georgeson MA, Freeman TCA, Scott-Samuel NE, Sub-pixel Accuracy: Psychophysical Validation of an Algorithm for Fine Positioning and Movement of Dots on Visual Displays. Vision Res. 1996 36(4): 605-612.

Strouthidis NG, Vinciotti V, Tucker AJ, Gardiner SK, Crabb DP and Garway-Heath, D. F. Structure and Function in Glaucoma: The Relationship between a Functional Visual Field Map and an Anatomic Retinal Map. Invest Ophthalmol Vis Sci. 2006 47: 5356-5362.

Verdon-Roe GM, Westcott MC, Viswanathan AC, Fitzke FW.Garway-Heath, D. F. Exploration of the psychophysics of a motion displacement hyperacuity stimulus. Invest Ophthalmol Vis Sci. 2006b. 47(11):4847-55.

* cited by examiner

Humphrey 24-2 locations superimposed on the retinal image

IOVS, December 2006, Vol 47, No. 12

| | | | 0 | 0 | 0 | 0 | | |
|---|---|---|---|---|---|---|---|---|
| | | .23 | .22 | | | 0 | 0 | |
| | .23 | .31 | 0 | 0 | 0 | 0 | 0 | 0 |
| | .23 | .25 | 0 | 0 | 0 | 0 | 0 | 0 |
| | .16 | (.14) | 0 | 0 | 0 | .20 | .16 | 0 |
| .39 | .39 | .41 | .32 | .20 | .36 | (.12) | 0 | |
| (.80) | (.75) | .61 | .20 | (.13) | 0 | | | |
| 1 | 1 | 0 | 0 | | | | | |
| 1 | 0 | | | | | | | |

Figure 5B

SUPRA-THRESHOLD TEST AND A SUB-PIXEL STRATEGY FOR USE IN MEASUREMENTS ACROSS THE FIELD OF VISION

FIELD OF THE INVENTION

The present invention relates to a supra-threshold test for use in detecting sensitivity loss across the field of vision, for example, to identify or investigate glaucoma, and a sub-pixel strategy for use in measurements across the field of vision.

BACKGROUND OF THE INVENTION

Glaucoma describes a group of conditions which have in common progressive optic neuropathy with associated patterns of visual field loss. There are various known techniques to detect the presence of visual field loss due to glaucoma. One such known technique is the Moorfields Motion Displacement Test (MDT) which has been developed by a collaboration between Moorfields Eye Hospital, London, the UCL Institute of Ophthalmology and City University London, see Fitzke et al 1987, Verdon-Roe et al 2006a and Verdon-Roe et al 2006b (CE Mark Registered Number CE 2006/0012, Date: 14 Jul. 2006, Manufacturer AC Viswanathan).

The Moorfields MDT involves the presentation of a pattern of multiple vertical lines. The software design permits direct loading of researcher defined bitmaps into members of the object-oriented bitmap class without the need for recompilation, see Viswanathan 2000. The lines are each scaled in size by an estimate of retinal ganglion cell density, see Garway-Heath et al 2000a. This does not apply to centrally placed lines, which are not scaled by retinal ganglion cell density, but are sized to be resistant to the effects of optical blur so that the test can be performed without refractive (spectacle) correction, see Verdon-Roe 2006a. The line coordinates are selected by application of the Garway-Heath anatomical-functional map to reduce the number of locations tested in optic disc sectors that are over-represented in conventional perimetry, see Garway-Heath et al 2000b.

During the Moorfields MDT, the viewer is asked to maintain their gaze on a specific (fixation) target for the duration of the test. The lines are subjected one at a time to a brief period of horizontal oscillation at a frequency of approximately 5 Hz, see Verdon-Roe et al 2000, and duration of 200 ms per cycle, see Westcott et al 2000. Each period of line oscillation presents a stimulus to the visual field. The viewer is asked to indicate whenever they detect such a stimulus. The overall test comprises a sequence of such line presentations (stimuli), where each location is activated in turn, generally in accordance with some randomised order, and the view provides feedback for each stimulus that they can observe.

FIg. 1A is a schematic illustration of the results from an MDT for a spatial pattern of 52 locations to match the Humphrey 24-2 visual field test pattern of standard automated perimetry (SAP). The small circles indicate locations where the user successfully responded to the stimulus at that location, while the crosses indicate locations at which the viewer did not respond to the stimulus. The duration of the test is approximately 90 seconds to allow for a stimulus to be presented once at each test location.

However, it has been found in practice that the response of a viewer is not completely reliable (repeatable). In particular, there is approximately a 5% chance that a healthy observer will miss any given stimulus. For a test sequence comprising 52 locations (and one presentation per location), there is an expected rate of 2.6 false negative responses per test sequence (where a response is regarded as false negative if it incorrectly fails to be seen).

Accordingly, it is known in supra-threshold vision tests such as the Moorfields MDT to have a retest strategy, whereby the overall test sequence includes repetitions of the stimulus for at least some locations. FIG. 1B illustrates one such retest strategy, which involves repeating the stimulus once for each test location—i.e. each location has a first presentation and a second presentation (usually not consecutively, but rather interspersed with stimuli at other locations). If the first presentation and the second presentation both give the same result (either both positive or both negative), this result is then accepted as correct for that location.

On the other hand, if the first presentation and the second presentation give different results, then a third presentation is performed for this location. This leads to three presentations at the relevant location, and the final outcome is taken on a majority basis. In effect, this means that the result always corresponds to the outcome of the third presentation, since this necessarily matches one of the earlier presentations.

The approach of FIGS. 1A and 1B represent a supra-threshold test, in that it measures whether or not a subject exceeds a predetermined threshold. Such a supra-threshold test is used for screening, in that individuals who exceed the predetermined threshold are suspected of having visual field damage, and can therefore be provided with further testing. This is to be contrasted with a threshold test, which measures the limit of sensitivity for a given subject. In other words, the outcome of a supra-threshold test is a spatial distribution of binary values (pass/fail), whereas the outcome of a threshold test is a spatial distribution of numerical values corresponding to the threshold of visual sensitivity at each location.

In addition, the approach of FIG. 1B is referred to as a supra-threshold 2/3 test, in that it measures whether a subject can or cannot see the stimulus on a majority 2 out of 3 basis. In contrast, the approach of FIG. 1A is referred to as a supra-threshold 1/1 test, because the conclusion is based on the findings of just a single measurement.

It will be appreciated that the retest strategy of FIG. 1B involves testing each location at least twice—more particularly, usually about 10% of the locations are tested three times, while the remaining locations are tested twice. The number of false negatives with this approach is much lower than compared with the approach of FIG. 1A (reduced by a factor of about 10), so that the results are more reliable. However, having to provide repeat stimuli at a given location increases the duration of the overall test (by a factor of just over two, if scaling by the number of activations). This raises the practical costs of administering the test, since for a given set of equipment and medical support staff, the number of subjects that can be tested in a given time period is reduced, It is therefore desirable to be able to reduce the time taken for administering a supra-threshold vision test such as the Moorfields MDT, but without compromising the statistical reliability of the test.

Another use for a motion displacement test is to measure the visual sensitivity of a subject across the field of vision. For example, the movement (amplitude of oscillation) of the stimulus can be made smaller and smaller until a threshold is reached beyond which the movement is no longer discernable to the subject. Such sensitivity measurements can be used both for detecting the presence of disease or other damage to the visual field, and/or to measuring the 'progression' (deterioration) of such disease/damage. The more finely the amplitude of the stimulus can be controlled, the greater the accuracy of the results that can be obtained.

In most test environments, an LCD monitor is located approximately 0.3-0.4 m away from the subject, a distance which provides a comfortable focus and also allows the screen of the monitor to occupy the area of field of the subject that is required for assessing glaucoma. At this distance, the visual resolution of the subject may exceed the pixel resolution of the monitor, especially in the centre of the field of vision, where retinal ganglion cell density is greatest. This limits the motion displacement thresholds that can be measured with such equipment. The situation is worse with young people, who have relatively higher retinal ganglion cell density.

Another way of making a stimulus presentation more difficult to see is to reduce the stimulus energy (area* luminance) see Verdon-Roe 2006b associated with the presentation, for example by reducing the area or luminance intensity of the stimulus line. In practice, it is common to use lower stimulus intensities for younger people to compensate for their increased motion displacement sensitivity. However, in some cases the threshold measurement of the subject remains above the resolution of the monitor. This makes it more difficult to track the progression of visual sensitivity for a single subject over longer periods.

A further concern with visual tests such as an MDT is that a subject must maintain fixation during the test in order to obtain reliable results. In other words, the eye being tested must look at a fixed location during the screen (otherwise the locations being tested will shift relative to the visual field). Most existing visual field tests provide some form of fixation target, such as a central dot or cross, to help the subject maintain fixation. Nevertheless, loss of fixation remains a problem in obtaining reliable test results.

SUMMARY OF THE INVENTION

One embodiment of the invention provides a method and apparatus for performing a supra-threshold test for detecting loss of sensitivity across a visual field of a subject. The method and apparatus present a stimulus at each location of a set of locations spread across the visual field; obtain for each stimulus a result indicating whether or not the stimulus was seen by the subject; and determine for each location whether or not to re-present a stimulus at that location. For a given location, the determining involves combining results obtained from multiple locations. The multiple locations are defined by a cluster associated with the given location. The cluster is determined based on the paths of optic nerve fibre bundles across the visual field.

Combining results from within a cluster associated with a given location allows a more reliable and/or quicker determination of whether or not the subject has passed the supra-threshold test for that location. In other words, a given level of reliability can be determined with less retesting than for conventional supra-threshold tests, which allows for faster and hence more cost-effective testing. It will be appreciated that the test results can be utilised by a clinician for helping to detect any loss of visual sensitivity across the field of vision. In one embodiment the supra-threshold test comprises a motion displacement test, but the supra-threshold test may also be applied to other testing methodologies.

One embodiment of the invention comprises providing a weights array corresponding to the cluster. Each location in the cluster is allocated a weight. The combining comprises filtering the results using the weights array. The filtered results are then examined to determine whether or not to re-present a stimulus at a given location by selecting locations having intermediate results above a first limit but below a second limit for re-presenting the stimulus. It will be appreciated that these intermediate results represent uncertainty, in that the relevant location does not have a clear seen or unseen status. Such uncertainty may arise, for example, because a presentation at the relevant location was unseen, but presentations at neighbouring, optically correlated locations, were all seen.

One embodiment of the invention further comprises adjusting stimulus intensity prior to performing a re-presentation of the stimulus. This can be used to control sensitivity and response.

One embodiment of the invention further comprises performing multiple cycles of said presenting, obtaining and determining. The cycles terminate if it is determined not to re-present the stimulus at any of the set of locations, or if a predetermined maximum number of cycles have been performed.

In one embodiment of the invention, for a given location (denoted as a primary location), the cluster for the primary location is determined by calculating a correlation between the primary location and other locations in the set of locations (denoted as secondary locations). The correlation between the primary location and a secondary location is calculated using a parameter based on the paths of optic nerve fibre bundles across the visual field that pass through or close to the primary location and the secondary location.

In one embodiment of the invention, the parameter is based on the angle between (i) a first optic nerve fibre bundle that passes through the primary location; and (ii) a second optic nerve fibre bundle that passes through the primary location. The angle between the first optic nerve fibre bundle and the second optic nerve fibre bundle is measured at the optic nerve head. The correlation is further based on the retinal distance between the primary location and the secondary location.

In one embodiment of the invention, a secondary location is added to the cluster for the primary location if the correlation between the primary location and the secondary location exceeds a predetermined threshold. A weight is determined for each secondary location in the cluster based on the correlation between that secondary location and the primary location.

It will be appreciated that other embodiments may utilise different and/or additional parameter(s) and techniques for calculating the correlation between different locations within the visual field.

One embodiment of the approach described herein provides an apparatus for performing a visual field test, wherein said apparatus is configured to provide a fixation target for a subject of the visual field test, wherein said fixation target comprises an image. Another embodiment provides an apparatus for performing a visual field test, wherein said apparatus is configured to provide a fixation target for a subject of the visual field test, wherein said fixation target comprises a substantially circular ring pattern which is approximately the same size as the human macular. The fixation targets of these embodiments may be utilised in conjunction with the various other embodiments described herein.

One embodiment of the invention provides an apparatus and a method for performing a motion displacement test across a visual field of a subject, wherein said motion displacement test involves presenting a stimulus comprising movement of a display feature. The method and apparatus include a liquid crystal display monitor (LCD) comprising a plurality of pixels, where each pixel comprises multiple sub-pixels, each sub-pixel being configured to output light of substantially the same colour. The method and the apparatus use sub-pixellation rendering for displaying the movement of said display feature.

In one embodiment, the sub-pixels in a given pixel all produce the same output energy (where energy can be considered a corresponding to overall luminosity or output, for example, as sub-pixel area multiplied by luminance). In general for a displacement test, the display feature (e.g. a vertical line) is held at a constant energy during the displacement. The threshold is related to the positional displacement of the stimulus energy relative to the background. This is facilitated by all the sub-pixels producing the same output energy, so that the display feature will then have a constant output energy at the different positions, providing it is displayed by illuminating the same number of sub-pixels. In one implementation, the sub-pixels all share the same intrinsic brightness as one another. In this case, a binary configuration may be used to control the sub-pixels—i.e. they are either on or off, where "on" corresponds to some fixed output level for the sub-pixel (such as the maximum output level for the pixel). In other embodiments, the intrinsic output energies of the sub-pixels may vary from one sub-pixel to another, but this is compensated for by arranging to drive each sub-pixel at an appropriate level on a gray-scale (so that all the sub-pixels then have the same output energy level).

Such an approach involving the use of sub-pixellation rendering can help to improve the high sensitivity end of the dynamic test range of the motion displacement text. For example, in one embodiment, the method and apparatus may present stimuli having a range of different displacements, wherein the displacement for at least one of the stimuli differs from the displacement for another one of the stimuli by a sub-pixel amount. In one particular implementation, stimuli are presented having an incremental step in displacement, wherein said incremental step corresponds to a sub-pixel spacing. Thus a first stimulus may be presented, and then a second stimulus, which has a larger displacement than the first stimulus, where the increment in displacement between the first and second stimulus corresponds to a sub-pixel spacing. The stimulus can continue to be increased in displacement using this sub-pixel spacing until it is seen by the subject of the test.

Such an approach helps to provide increased precision to measure test threshold, because the use of sub-pixellation can be considering as improving the resolution of the LCD monitor, thereby allowing finer granularity in the control of the displacement. This in turn permits a more accurate assessment of the displacement at which a stimulus first becomes visible, especially for small displacements (when the granularity of the pixel display is most significant).

In one embodiment, the display feature comprises a vertical line, and wherein said movement is horizontal movement of said vertical line. However, it will be appreciated that other implementations may use different shapes or designs for the display features (which may potentially differ across the field of view), and/or different directions of movement (which may not necessarily represent just a linear displacement). In one embodiment, the sub-pixels are evenly spaced in a direction parallel to the direction of said movement of the display feature (e.g. horizontally, in the above case). This helps to ensure a smoothness of movement when utilising the sub-pixellation strategy. In one embodiment, each sub-pixel is configured to output white light. Other embodiments however might output a different colour of light, for example, the sub-pixels might all be red.

One embodiment of the present invention provides a computer program for implementing a method such as described above. The computer program comprises computer program instructions may be provided on a computer readable storage medium, such as an optical disk (CD or DVD) or flash memory. The computer program may be loaded into a computer memory from such a storage medium, or may be downloaded into the computer memory over a network, such as the Internet. The apparatus or computer receiving the computer program comprises one or more processors for executing the computer program, which comprises instructions that cause the computer to implement a method such as described above. The test may be performed using a screen that is an integral part of the computer (such as a laptop screen), or alternatively the computer may control the display on some separate apparatus to provide the test. In addition, some or all of the functionality may be implemented by special-purpose hardware (rather than by running software on general purpose hardware).

BRIEF DESCRIPTION OF THE DRAWINGS

FIGS. 5A and 5B illustrate the calculation of the estimated probability of true damage for various locations within the visual field in accordance with one embodiment of the invention.

DETAILED DESCRIPTION

The present approach provides a suprathreshold visual field test in which cluster analysis is used for the retest strategy, in other words for determining which locations to retest and which locations not to retest. The cluster analysis incorporates physiological information concerning the spatial arrangement of optical nerve fibres across the retina. In particular, it is recognised that that if a given optical nerve fibre is damaged, then damage is more likely at test locations clustered on or close to the path of the optical nerve fibre. Conversely, if a given optical nerve fibre is healthy and working properly, this correct operation is likewise more likely at test locations clustered on or close to the path of the optical nerve fibre.

According to the present approach, locations in a healthy cluster are immediately eliminated from retest, whereas large points in a cluster that have been flagged as damaged during an initial part of the test sequence are isolated and regarded as defective. The (re)testing is then limited to testing only locations along the edges of a defect (where a single point is regarded as representing its own edge), irrespective of whether or not such edge locations were initially flagged as being damaged.

The cluster analysis utilises correlations between locations in the view field by application of anatomical and functional relationships. Such correlations can be determined from a mapping of the optic nerve head (ONH.) across the retina, such as provided by Strouthidis et al (2006) and Garway-Heath et al (2000b). Such a map involves two parameters for every test location (TL) in order to determine a relationship between a primary test location and a secondary test location (representing the other TLs in the visual field). The first parameter is derived by tracking the nerve fibre bundle on which the primary TL sits back to the optic nerve head, and likewise by tracking the nerve fibre bundle on which the secondary TL sits back to the optic nerve head. The first parameter then reflects the angle between these two nerve fibre bundles at the ONH. The second parameter is the Euclidean distance between the primary TL and the secondary TL. Denoting the first parameter as ONHd and the second parameter as RETd, then an expression for the correlation between the primary TL and the secondary TL can be given as:

$$FC=(0.0029)*ONHd-(0.0077)*RETd+(0.0001)*ONHd*RETd \quad \text{(Eq. 1)}$$

Figure 2:
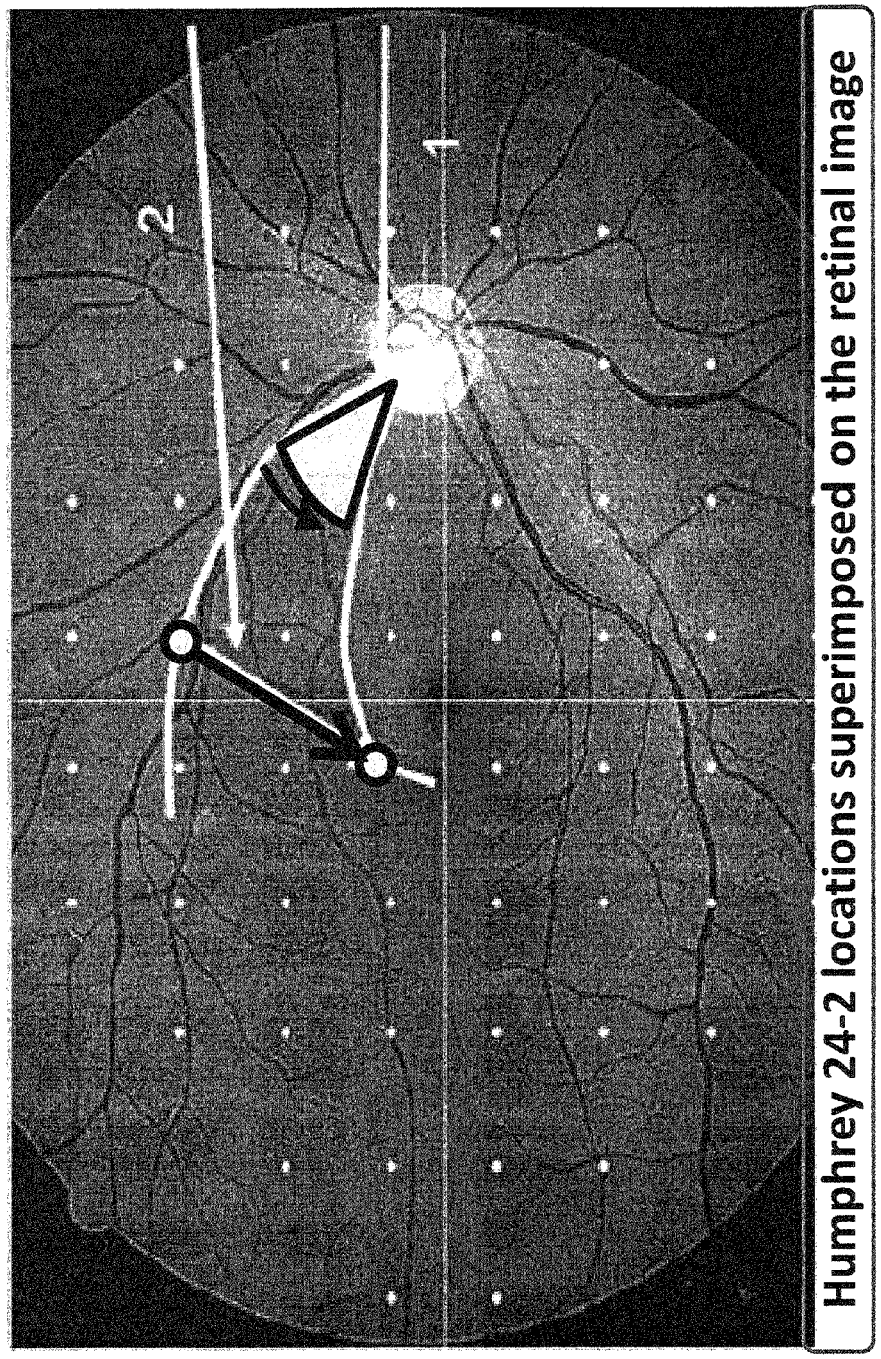
FIG. 2 depicts an image of the optic nerve head and optic nerve fibre bundles with superimposed test locations, and illustrates the two parameters used for determining the correlation in retinal sensitivity between two different test locations in accordance with one embodiment of the invention.

FIG. 2 illustrates the determination of the above correlation. In particular, FIG. 2 shows the set of test locations according to the Humphrey 24-2 visual field test pattern superimposed on a retinal image from Strouthidis et al. The large white circle represents the optic nerve head, while the dark lines correspond to optic nerve fibre bundles spreading across the retina. The two test locations marked by larger black dots (and linked by a large black arrow) correspond to examples of a primary and secondary test location. The white lines passing through the black dots represent the paths of the particular optic nerve fibre bundles that pass closest to the primary and secondary test locations.

The first and second white arrows in FIG. 2 (as per the white numbering) indicate the first and second parameters respectively from Equation 1 above. In particular, the first parameter is dependent on the angle indicate between the two nerve fibre bundles shown in white lines at the optic nerve head, as represented by the angular segment and corresponding black arrow. The second parameter corresponds to the length of the black arrow between the primary and secondary test locations.

Figure 3:
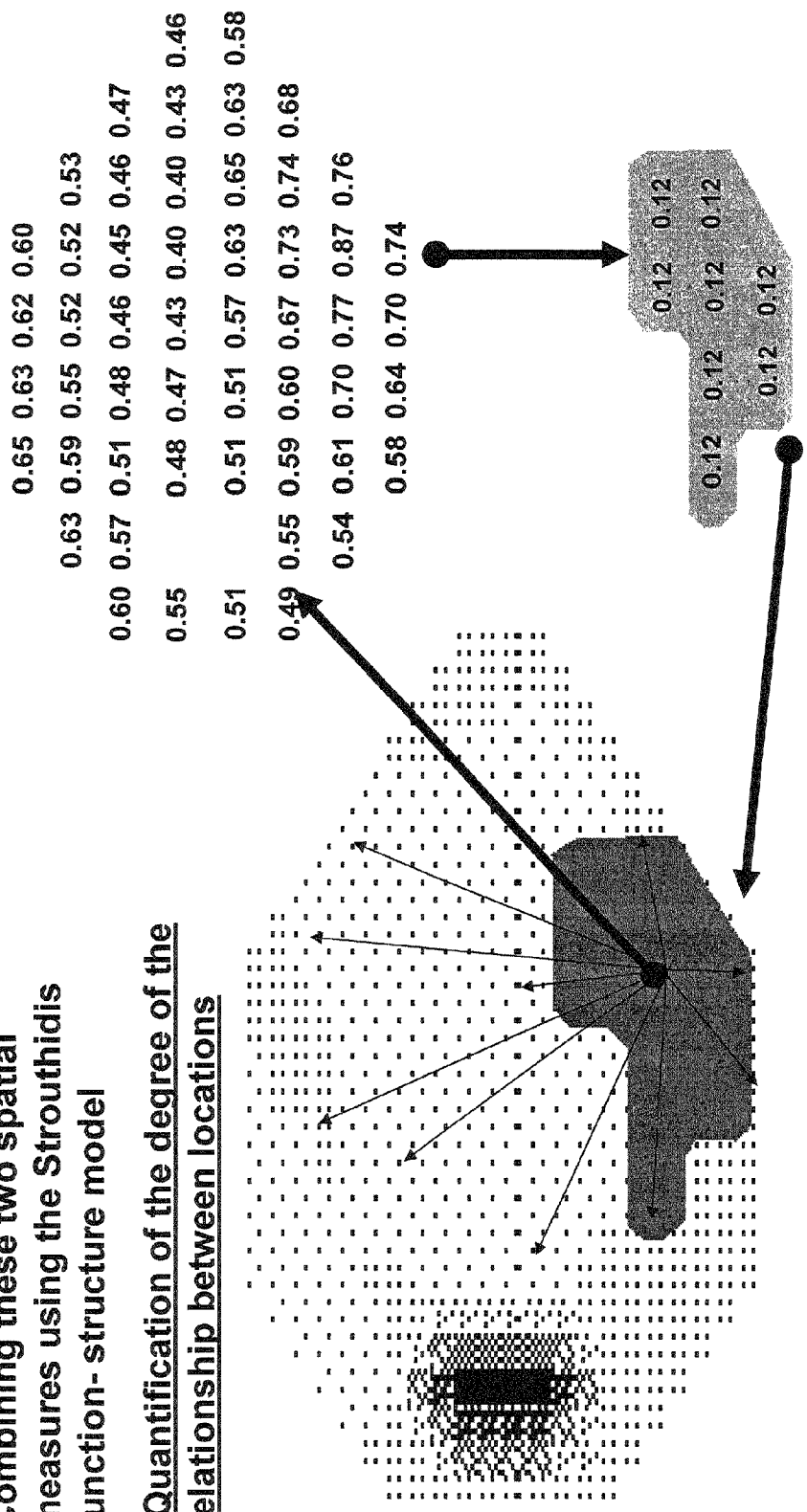
FIG. 3 is a schematic illustration of how to determine a set of cluster weights for locations associated with a given test location in accordance with one embodiment of the invention.

FIG. 3 illustrates an example set of correlations calculated for an eye. (Note that the ONH in FIG. 3 is depicted to the left rather than to the right). In particular, the primary TL in FIG. 3 is as indicated in the schematic representation of the eye to the left of FIG. 3, which serves as the basis for the set of arrows propagating to (example) secondary locations. The numerical set of calculated correlations for this primary location is shown top right, where the correlations range from 0.4 up to 0.87. Those 8 locations having a correlation value equal to or greater than 0.7 are shown in bold, and correspond to the subset of locations shown bottom right in FIG. 3. This subset can be regarded as a cluster of locations with respect to the selected primary location. The spatial extent of this cluster is also indicated in the schematic representation to the left of FIG. 3.

The numbers specified in the cluster to the bottom right of FIG. 3 correspond to weights within the cluster. The weights sum to unity across the cluster as a whole, and reflect the strength of correlation between the primary location and each of the secondary test locations within the cluster (renormalisation). In particular, the higher the weight shown for a given secondary test location, the greater the correlation between that secondary test location and the primary test location. This pattern or cluster of weights will be referred to herein as a weightings array (WA).

Figure 4:
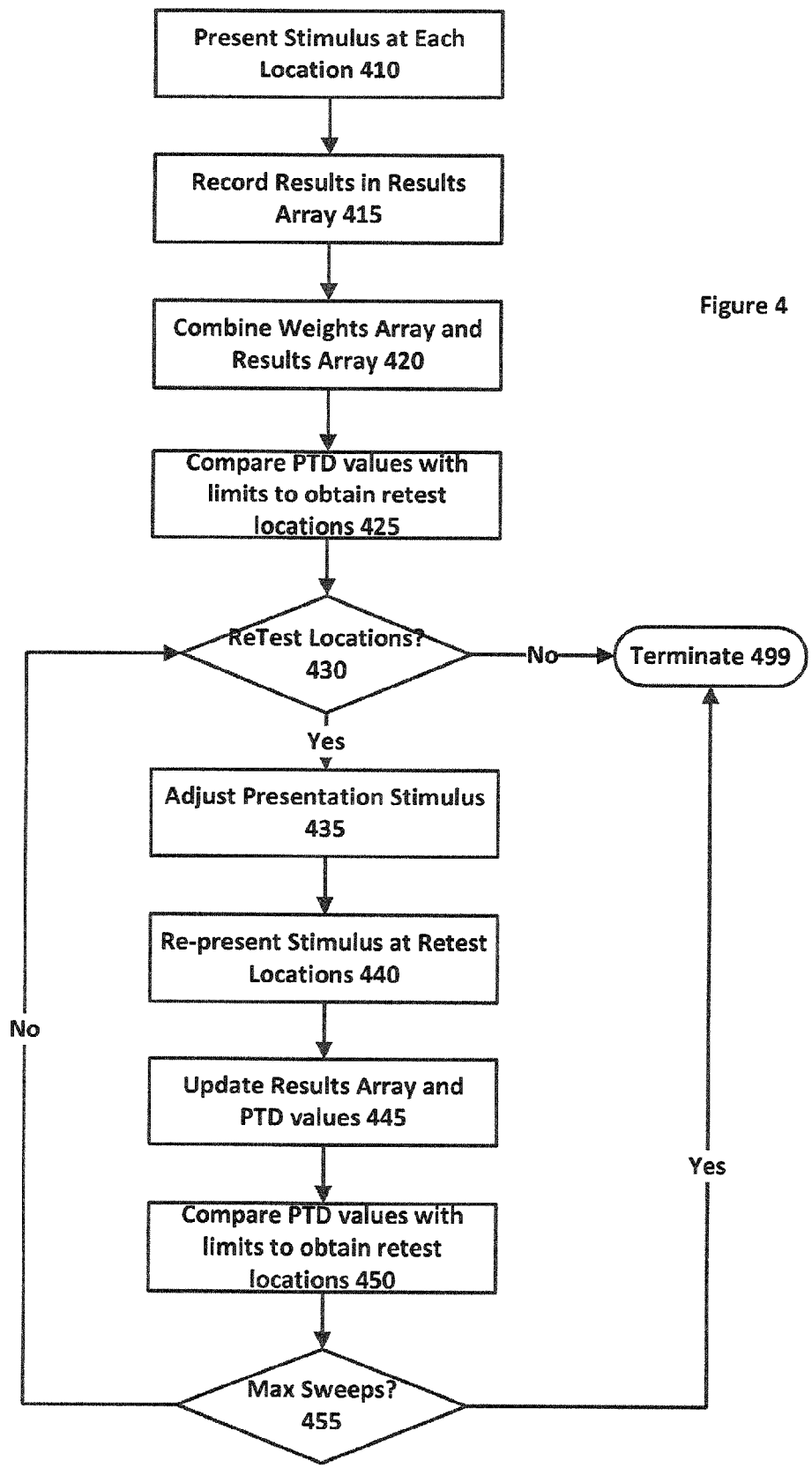
FIG. 4 is a flowchart illustrating a procedure for use in testing for visual field damage or degradation in accordance with one embodiment of the invention.

FIG. 4 is a flowchart illustrating a method for performing a suprathreshold test for an MDT in accordance with one embodiment of the invention. In operation 410, a stimulus is presented at each of the test locations. The stimulus may be set at an intensity corresponding to 95% of the normal cut-off value. The results (yes/no) from all the different locations are then saved into a results array (RA) (operation 415).

Next, the weights array and the results array are combined as part of the cluster analysis to give a value for each location that represents the estimated probability of true damage (PTD) (operation 420). The PTD values are now examined with respect to limits to identify locations for retest (operation 425). In particular, locations that have a high estimated PDT (above a first limit, T1), and those locations that have a low estimated PDT (below a second limit, T2), where T1>T2, are not selected for retesting. Rather, the only locations selected for retesting have a value of PDT such that T1>PDT>T2. If no locations satisfy this criterion, then the test terminates (operations 430, 499).

For those locations selected for retesting, the presentation intensity is adjusted (operation 435) (as explained in more detail below) and the stimulus is presented at these locations again at this new intensity level (operation 440). The new (retest) results are recorded and combined with the previous results (as explained in more detail below) to produce an updated version of the results array, and from that, an updated set of estimated PTD values (operation 445). These estimated PDT values are now re-examined (operation 450) with respect to the restraint such that those locations selected for retesting (i) have a value of PDT such that T1>PDT>T2 (as per operation 425), and (b) do not have two or more presentations giving the same result—i.e. both seen or both unseen.

A determination is now made as to whether a maximum number of sweeps (loops or cycles) has been performed (operation 455). In one embodiment, the maximum number of sweeps is set at 5, but other embodiments may have different settings. If maximum number of sweeps has not been performed, the processing loops back to operation 430, in which a set of retest locations is determined by thresholding the estimated PTD values. This processing loop then continues as previously described through operations 435, 440, 445 and 450 until either no retest locations are determined at operation 430, or the maximum number of sweeps is reached at operation 455, in which case processing terminates at operation 499.

In one embodiment, for those presentations which are above the 95% limit of normality, a 2/3 criterion is applied—i.e. 2 unseen presentations above this level=failed, while 2 seen presentations above this level=passed. Therefore a maximum of four presentations should occur at any given location. This criterion can be considered as part of operation 430 (select retest locations) or operation 455 (max sweeps). In other embodiments, a different criterion might be applied, such as 3/5.

The result for each stimulus, i.e. for each test at a given location, is binary in nature—Yes (positive) if the viewer observed the stimulus, No (negative) if they did not. The result can be considered as dependent on the presentation level, denoted as $\beta$, which represents the chance of a normal or average observer seeing a presentation at that intensity level. A value of $\beta$ is recorded in the results array if the presentation is unseen, and a value of $1-\beta$ is recorded in the results array if the presentation is unseen. For example, if the presentation intensity is set to a 95% level, then the results array will contain the value 0.05 at the locations where the presentation was seen, and 0.95 at the locations where the presentation was not seen.

For a given primary location, the estimated probability of true damage is calculated (as per operation 420) by multiplying together the results array and the weights array, and then summing the results. N.B. due to renormalisation, test locations outside the cluster for any given primary location will have a weight value of 0. For example, in FIG. 3, the weights array values for the cluster are shown bottom right, while the remaining locations are zero (these correspond to positions top right in FIG. 3 that do not have their correlation shown in bold).

We can therefore represent the calculation of the estimated PTD for a given primary location as:

$$\Sigma RA(TL) \times WA(TL) \qquad \text{Eq. (2)}$$

where the summation is performed over all test locations, RA(TL) represents the result value for the given test location, and WA(TL) represents the weight for the given test location (for the relevant primary location).

The cluster analysis combines information from multiple related test locations according to the physiological relationship between the retinal sensitivity values at these test locations (based on the pattern of optic nerve fibre bundles). This provides a statistically more robust set of results, because the aggregation of data can compensate for individual (isolated) random response errors by the viewer, but with a reduced amount of testing compared with the approach of FIG. 1B (for a given level of statistical accuracy).

In one embodiment, the limits T1 and T2 used at operation 425 for determining retest locations are fixed prior to testing and not altered during the testing itself. The limit T2 is set for each primary location so that if a single, isolated stimulus is missed (not seen) at the primary location, then this should always be retested. In other words, the results array is filled with $\beta$ at the primary location and $1-\beta$ elsewhere, and a PDT value is calculated for this primary location in accordance with Eq. 2 above. The limit T2 is then set below the resulting PDT value to ensure that an isolated test miss at this primary test location will always trigger a retest. The upper limit (T1) can be set using the converse procedure, i.e. by assuming a user sees a single, isolated stimulus, so that the results array is filled with $1-\beta$ at the primary location and $\beta$ elsewhere. The limit T1 is then set above the resulting PDT value to ensure that an isolated detection at this primary test location will always trigger a retest, but large clusters of missed locations would be eliminated.

In one embodiment, the starting intensity is set to the 95% cut-off, as for a conventional supra-threshold test. The intensity of the stimulus may then be adjusted for following sweeps as per operation 435. In one particular embodiment, if a test location is selected for retesting, the intensity of the stimulus is adjusted according to the number of presentations which have already been presented at this test location. Thus for the second presentation, the intensity is increased above the 95% cut-off such that there is only a 1% chance for a normal subject to miss both presentations. On the third presentation, the stimulus intensity is shifted down below the 95% cut-off to increase sensitivity, so that a borderline abnormal subject will have <50% of missing both presentation number 1 and presentation number 3. The fourth presentation is at the 95% level again (as for any additional sweeps).

As discussed above, after the first sweep, the results array contains the values of 0.05 and 0.95 according to whether a presentation was seen or unseen (respectively), based on an initial 95% stimulus intensity level. For subsequent presentations, only some of the test locations are retested and also the stimulus intensity level may vary. These factors are taken into consideration when updating the results array at operation 445. In particular, the value of the results array for a given test location is given by:

$$(\Sigma_i R(i) K(i))/(\Sigma_i K(i)) \qquad \text{Eq. (3)}$$

where the sum over index i is from 1 to n, where n is the number of sweeps performed, $K(i)=1$ if the test location is presented (i.e. tested or retested) in sweep i, and $K(i)=0$ if the test location is not tested (presented) in sweep i, and R(i) has the value of $\beta$ if the presentation for sweep i is unseen, and a value of $1-\beta$ is the presentation for sweep i is not seen, as described above, with $R(i)=0$ if there is no presentation at that test location for sweep i.

When the test has completed (at operation 499), those locations that have an estimated probability of true damage at or above the associated upper bound (>T1) are flagged as failed. All other locations are considered to have passed the test.

Figure 5A:
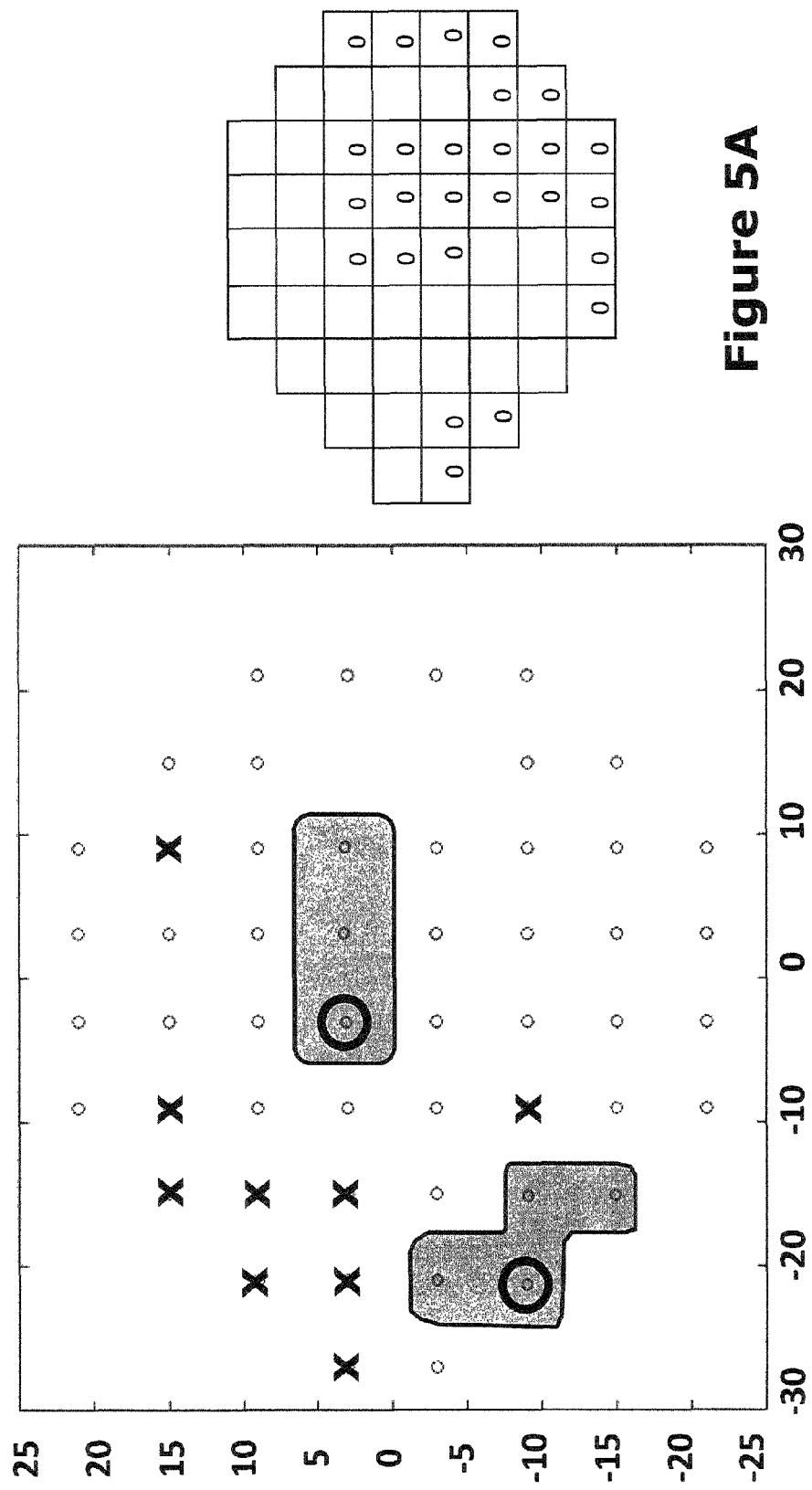

FIGS. 5A and 5B illustrate an example of the use of the method shown in FIG. 4. In particular, FIG. 5A shows the results of making a set of presentations at the specified locations. The left-hand side of FIG. 5A depicts the pattern of testing. If a presentation is seen at a given location, then the location is represented by a small circle, while if the presentation is not seen at the given location, the location is represented by a cross. Two test locations having a larger circle and shaded background. The shaded background represents the cluster of secondary locations associated with the primary location marked by the larger circle. In both cases the results are consistent throughout the cluster, namely the presentation was seen.

The table on the right-hand side of FIG. 5 corresponds to the test pattern shown on the left-hand side of the diagram and can be considered as corresponding to the estimated probability of true damage as discussed above in relation to FIG. 4. Those locations marked with a zero represent locations for which the cluster associated with the relevant location contains only locations for which the presentation was seen. These locations are marked with a zero since they can be considered as necessarily passing the test.

FIG. 5B illustrates the complete results array. Those locations marked with a one represent locations for which the cluster associated with the relevant location contains only locations for which the presentation was unseen. These locations are marked with a one since they can be considered as necessarily failing the test. The remaining locations (marked with neither one nor zero) represent intermediate locations for which inconsistent results were obtained in the cluster—i.e. not all seen or all unseen.

The estimated probability of true damage for these intermediate locations lies between 0 and 1. In the present case, the boundaries of PDT for re-testing are set at 0.15 and 0.7 (i.e. T1=0.7 and T2=0.15). As a consequence of these boundaries, the circled locations in FIG. 5B are not tested, since they are considered as being close enough to zero or unity to provide a reliable result. In other words, although the cluster associated with the circled locations contained a mixture of results (seen/unseen), the preponderance of the results (having regard to weighting within the cluster) one way or the other to determine whether or not the primary location should be regarded as seen or unseen.

The only locations retested from FIG. 5B are those at the remaining 16 locations—i.e. those that are not circled or marked with 0 or 1. It will be appreciated that this represents a significant reduction in the number of locations to be retested (compared, for example, with the approach illustrated in FIG. 1B), and hence allows faster testing, while at the same time providing reliable results.

The approach described herein has been implemented in conjunction with the Moorfields MDT, which is a laptop-based, multi-location test with 32 white line stimuli presented on a grey background of constant Michelson contrast of 85%, see Verdon-Roe et al 2006b. Each of the line stimuli is scaled in size according to local estimates of retinal ganglion cell density. The stimulus is repeatedly shifted by a discrete displacement and then restored in position so as to general an oscillation perpendicular to the length axis of the stimulus lines. The amplitude of the oscillation can be modulated. A threshold may be determined as the smallest discernable displacement, measured in minutes of arc.

A set of correlation filters were determined using the approach described above in relation to Equation 1 and FIG. 3. The centre-point of each line stimulus was used for calculating the retinal distance between each stimulus. A correlation cut-off of 0.65 was used to determine those locations forming the cluster about any given cluster. This is slightly lower than the example of FIG. 3 (which took a cut-off of 0.7) because there are fewer test locations for the current configuration of the Moorfields MDT (32 compared with the 52 test locations shown in FIG. 3). This cut-off level also ensured that each cluster contained at least one secondary location (in addition to the primary location). Note that as an additional constraint, clusters were prevented from extending across the horizontal meridian (which can be seen in FIG. 2 to represent a clear demarcation between different sets of optic nerve fibre bundles). The values of the T1 and T2 were set at 0.7 and 0.18 respectively as acceptable global limits of restraint on the PTD values (as per operation 425).

A pilot study was performed involving 13 mild to moderate glaucoma patients with 13 age-matched controls. The ages ranged from 31 years to 71 years, with an average age of 66.5 years. The mean optical defect for the patients had an average value of −4.1 dB, with a range of −0.5 to −8.8 dB. The patients were evaluated according to four different strategies:

a) standard automated periphery (SAP) using the Swedish Interactive Thresholding Algorithm (SITA). SITA is understood to involve neighbouring locations in its thresholding calculations.
b) MDT using conventional supra-threshold (1/1)—as per FIG. 1A
c) MDT using conventional supra-threshold (2/3)—as per FIG. 1B
d) MDT using the enhanced supra-threshold technique (ESTA) described herein.

Figure 6:
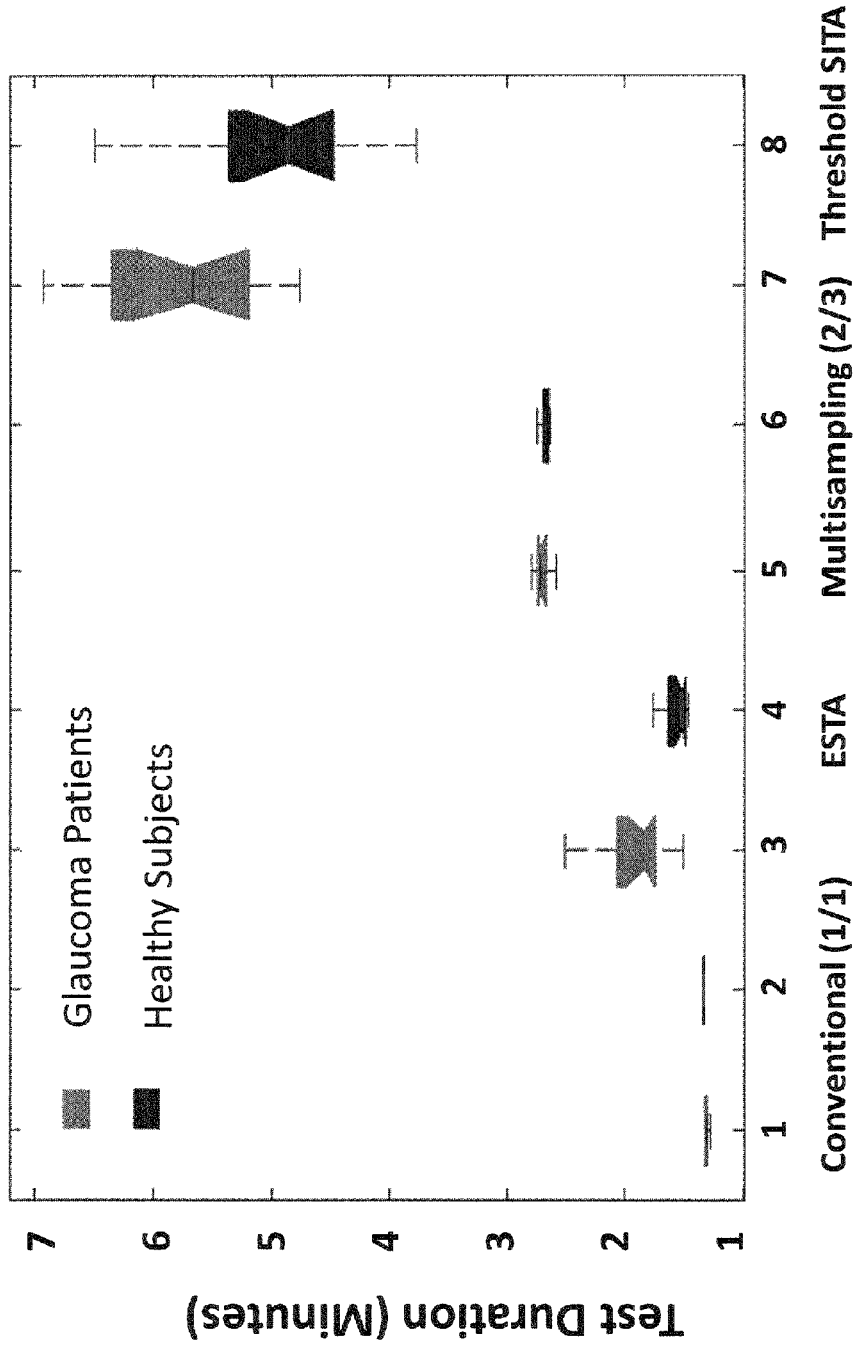
FIG. 6 is a graph plotting experimental results indicating the test duration for testing according to various strategies.

FIG. 6 illustrates the test durations in minutes for performing the above four tests. It can be seen that the conventional supra-threshold (1/1) approach for MDT is the fastest approach, as would be expected, since it only involves testing each location a single time. MDT using conventional supra-threshold (2/3) takes significantly longer to obtain results.

The approach described herein (denoted as ESTA in FIG. 4) can be seen to be slower than the conventional supra-threshold (1/1) approach, but significantly faster than MDT using conventional supra-threshold (2/3). All three of the MDT tests are much faster than the SAP SITA testing.

It is also noticeable that whereas the conventional supra-threshold tests, both (1/1) and (2/3), have approximately equal duration for both healthy and non-healthy patients, the ESTA approach is clearly quicker for healthy patients than for non-healthy patients. This can be attributed to the fact that unseen presentations for healthy patients will generally occur on a random (spatial) basis. The ESTA algorithm averages across physiologically related test locations, and hence is effective at discounting such isolated (random) errors without the need for further retesting. Where retesting does occur in ESTA, it has a greater likelihood of reflecting true damage to the visual field, rather than accidental omissions by a healthy subject.

Table 1 presents some reliability results for the above four tests, and also the average test time. The reliability results comprise the number of 2-point fails, i.e. test subjects which fail to see the stimulus at two or more locations. It will be appreciated that healthy subjects would not be expected to fall into this category (they should see the stimulus at all locations), while persons with visual field damage generally will represent 2-point fails. It can be seen from Table 1 that 3 of the four methods gave identical results concerning 2-point fails. The only method that gave different results was the MDT using conventional supra-threshold (2/3), which corrected identified one additional patient as a 2-point fail, but also incorrectly identified one healthy subject as a 2-point fail.

TABLE 1

| | Reliability (2-point fail) | | |
|---|---|---|---|
| Type | Patients | Healthy Subjects | Average Test Time |
| supra-threshold (1/1) | 12/13 | 0/13 | 1.2 minutes |
| ESTA | 12/13 | 0/13 | 1.6 minutes |
| supra-threshold (2/3) | 13/13 | 1/13 | 2.8 minutes |
| SITA (threshold) | 12/13 | 0/13 | 5.9 minutes |

Table 2 provides further information on reliability, in particular regarding the total number of missed locations summed across all subjects for the various technique. It will be appreciated that ideally the healthy subjects should have zero missed locations, while the number of missed locations for the patients will depend on the extent of visual field damage. It can be seen from Table 2 the total number of missed locations for the patients shows relatively little variability across the different techniques. However, the number of missed locations for healthy subjects shows more variability (both in absolute and relative terms). The supra-threshold (1/1) technique gives the greatest number of missed locations for healthy patients and so can be regarded (from this perspective) as the least reliable test. The supra-threshold (2/3) approach gives a slightly lower number of missed locations for healthy patients, while ESTA gives a still lower number of missed locations for healthy patients. Accordingly, ESTA appears to perform better than existing MDT supra-threshold tests. The best result in this test (lowest number of missed locations for healthy patients) is achieved by SAP SITA, albeit with a much longer testing time.

TABLE 2

Reliability (Total Number of Missed Locations)

| Type | Patients | Healthy Subjects | Average Test Time |
|---|---|---|---|
| supra-threshold (1/1) | 67 | 6 | 1.2 minutes |
| ESTA | 69 | 3 | 1.6 minutes |
| supra-threshold (2/3) | 66 | 5 | 2.8 minutes |
| SITA (threshold) | 68 | 1 | 5.9 minutes |

Figure 1A:
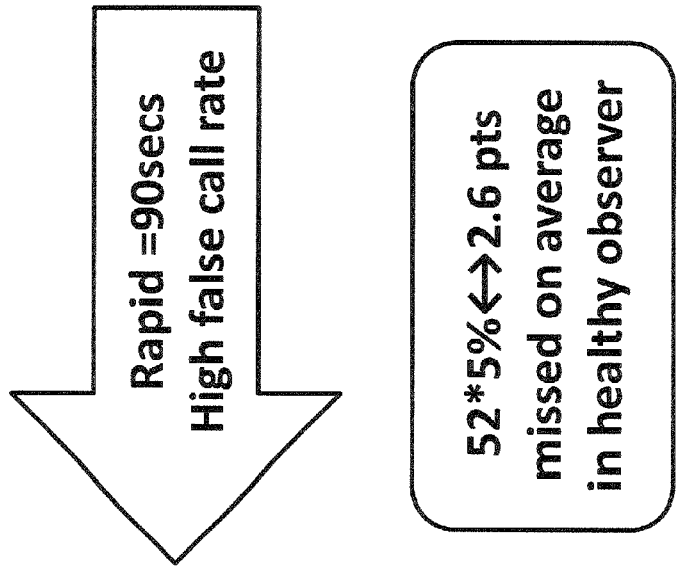
FIGS. 1A and 1B illustrate two known retest strategies used in a suprathreshold visual field test for detecting visual field damage.
Figure 1A:
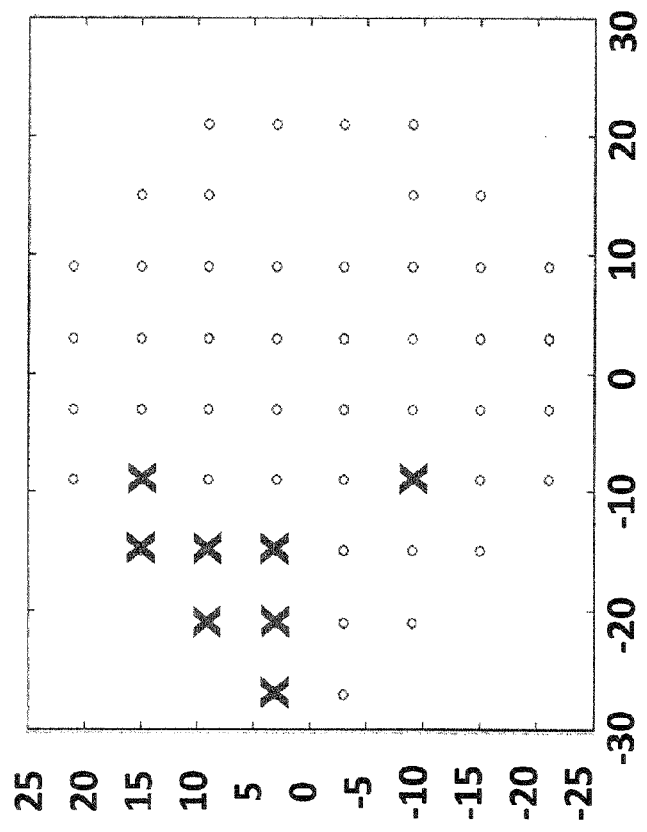
Figure 1B:
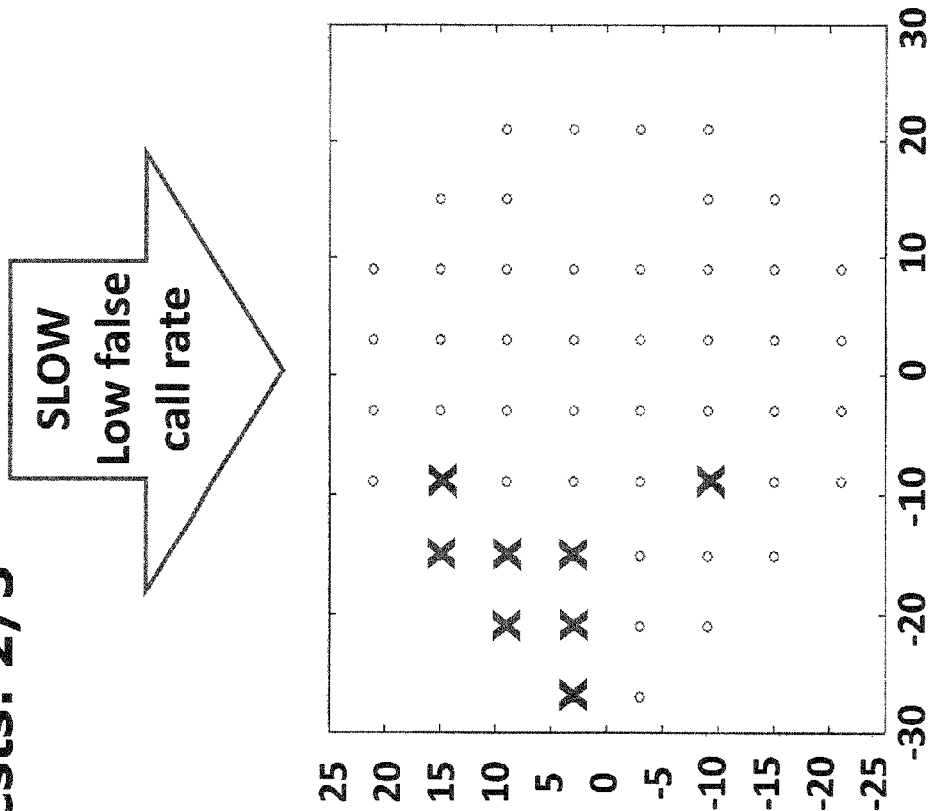
Figure 1B:
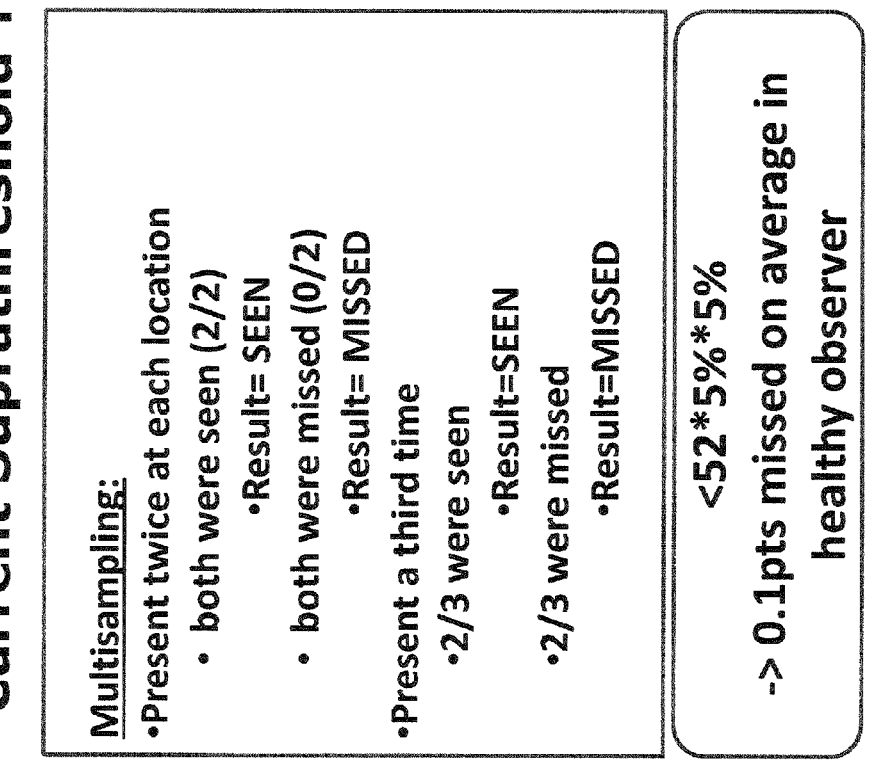

Considering now spatial accuracy, there are 13×32=416 test locations for the set of glaucoma patients. Taking the SAP SITA locations as the bench-mark, ESTA disagreed with the SAP SITA results in only 37 out of the 416 test locations (=8.8%). In contrast, the supra-threshold 2/3 test disagreed in 40 out of 416 test locations (=9.6%), and the supra-threshold 1/1 test disagreed in 49 out of 416 test locations (=11.7%). This indicates that ESTA provides more reliable results than conventional supra-threshold tests, such as shown in FIGS. 1A and 1B.

Although the above supra-threshold approach has been described primarily in the context of a motion displacement test (MDT) it will be appreciated that the same supra-threshold approach may be utilised in other techniques for testing for visual degradation or damage across a visual field. In addition, although the above approach has been described primarily in the context of detecting damage, i.e. by providing a yes/no determination for each location, it can also be utilised for measuring the performance level of different locations. One way of achieving this would be to perform the above method for detection at a series of different intensity levels (sometimes referred to as a staircase model). The intensity level at which the results transitioned from detection to non-detection at a given location would then provide a measure of the sensitivity (damage or degradation) at that location. Furthermore, although the above approach has been described primarily in the context of testing for glaucoma, it will appreciated that it could also be used in any other investigations of the sensitivity visual field (degraded or otherwise).

As discussed above, another concern with visual testing concerns provide an fixation target. Conventional fixation targets generally comprise a cross or a dot at the point of fixation. However, one embodiment of the present invention utilises an image, such as a bit map or similar, as the fixation target. Such an image might represent, for example, a cartoon character, and hence provide a highly effect fixation target for children. Another possibility is that the fixation target comprises some form of circular ring target, which is easier to see for people with macular generation than a cross or dot.

As mentioned above, one of the difficulties faced by motion displacement tests for measuring thresholds of vision, monitoring progression accurately, and so on, is that the the visual resolution of the test subject is greater than the pixel resolution of conventional LCD monitors, at least for some locations in the visual field. As will now be described, one way of addressing this problem is through the use of a sub-pixellation strategy.

Sub-pixel rendering was described by IBM in 1988 (see U.S. Pat. No. 5,341,153) and exploits the fact that each pixel of a monitor display usually comprises a spatial arrangement of three sub-pixels, corresponding to the three colours red (R), green (G) and blue (B). Providing sub-pixel accuracy of control for cathode ray tube (CRT) monitors is known in visual experiments, see for example Georgeson et al, 1996. This is achieved by suitably adjusting the intensity of neighbouring pixels. For example, let us assume that a row line of 5 pixels is represented by intensities (0, 0, 1, 0.5, 0), with this row being repeated multiple times to define a vertical line on the screen. If each row is changed to (0, 0.5, 1, 0, 0), this may appear to the viewer as a sub-pixel change (horizontal shift) in position of the vertical line.

Sub-pixellation techniques are also known for LCD monitors. These exploit the fact that each pixel of a conventional LCD monitor comprises a spatial arrangement of three sub-pixels, corresponding to the three colours red (R), green (G) and blue (B). Some display programs, such as ClearType™ from Microsoft Corporation, exploit this form of sub-pixellati on technique.

It has been found however that such conventional LCD sub-pixellation techniques are inappropriate for visual tests, such as the MDT. In particular, the sub-pixellation techniques are known to cause colour artefacts (since they selectively illuminate sub-pixels of different colours), which can be distracting in a visual test. Furthermore, the eye does not have a uniform sensitivity across all colours, so that the variation in colour caused by such a sub-pixellation technique may impact whether or not a given presentation is seen. This may then give a less reliable result for visual sensitivity, since the visibility of a presentation will be dependent on the colours arising from the sub-pixellation rendering.

One embodiment of the present invention therefore utilises a monochromatic LCD monitor in which each pixel comprises three sub-pixels, all the sub-pixels being white and of equivalent 'energy' (area*luminance), see Verdon-Roe 2006b. One example of such a monitor is the EIZO GS 521 monochromatic monitor, available from Eizo Nanao Corporation of Ishikawa, Japan (see www.eizo.com/global). The sub-pixellation which can be achieved with such a monitor avoids the colour artefacts of conventional colour LCD monitors, but rather ensures that there is a constant stimulus energy for all displacements fulfilling the requirements of the theshold energy displacement (TED) law see Verdon-Roe 2006b.

(The stimulus energy is defined according to:

ENERGY=([STIMULUS AREA]*[STIMULUS LUMINANCE−BACKGROUND LUMINANCE]) and the TED law specifies: $T=K\sqrt{E}$, where $T$=MDT THRESHOLD, $K$=CONSTANT, and $E$=STIMULUS ENERGY]).

As an example of a sub-pixellation strategy, consider the following row of 4 pixels, each comprising 3 sub-pixels: (0, 0, 0|0, 0, 0|1, 1, 1|0, 0, 0). Again, this will lead to a vertical line if the same pattern of pixels is repeated in multiple rows. The vertical line can be shifted one-third of a pixel to the left (for example) by altering the subpixel values to (0, 0, 0|0, 0, 1|1, 1, 0|0, 0, 0). Note that such a change provides much finer control of the line location than moving the line one whole pixel at a time, but without introducing any colour artefacts (since all the sub-pixels are white). A further degree of control may be achieved by having suitable intensity variations. For example, the following row of pixels might be considered as intermediate the above two line positions (0, 0, 0|0, 0, 0.5|1, 1, 0.5|0, 0, 0). This enhanced control of stimulus location allows the presentation of a stimulus with a smaller (or more accurately controlled) amplitude of oscillation, and hence provides a more sensitive and more accurate measurement of visual sensitivity.

Considering now the sub-pixellation strategy in more detail, the pixel size of standard monitors limits the test resolution for measuring thresholds in the central field where retinal ganglion cell (RGC) density is highest. The results of one "orientation" study have found that some locations showed "all seen" responses—in other words, the smallest displacement could always be seen (Verdon-Roe et al 2006c). This particularly applied to the central locations but also occurred along the mid-line in subjects of all ages. There were also "all seen" responses scattered across the field of view in some young subjects (<40 years age). The mid-line effect was attributed to the horizontal streak and the effects of attention, which is foveally driven (Anderson et al 1992; Hock et al 1998). The pattern of "all seen" response may also be explained by the variation of receptive field size with eccentricity.

The problem of the "all seen" responses can be partly overcome by reducing the size of the stimuli along the mid-line and scaling the stimuli according to the physiological reduction in RGC with age, for example, by adopting three age bands: 21-40; 41-60; 61+ years. The central stimuli for the case-finding version, i.e. threshold test, version were scaled to be resistant to the effects of refractive blur (Verdon Roe GM, 2006a), although for the monitoring of glaucoma it may be better to scale the central stimuli by estimates of RGC density and test with optical correction. The scaling by age-band has been found to be partly successful (Moosavi 2008), but it would be beneficial to have a constant stimulus size for the estimate of normative values across the ages if possible.

The sub-pixel strategy described herein has been developed to help address the problems of "all seen" responses and having to scale by age. The sub-pixel strategy helps to increase the number of incremental steps within the dynamic range of the MMDT stimulus so as to:
(i) enable measurement of MMDT thresholds in the central field of vision.
(ii) enable measurement of MMDT thresholds across the field of vision using the same stimulus sizes across all age groups, thereby strengthening our understanding of normative values.
(iii) extend the role of the MMDT to include the monitoring of glaucoma progression.

The glaucoma detection technology used for case finding is usually different from the more expensive monitoring technology used in hospital care. This results in time being wasted by having to establish new baseline measurements for patients on referral to the hospital system. Furthermore, the use of different technology in primary and secondary care is a barrier to the shared care of stable glaucoma. In contrast, the approach described herein provides an affordable technology that is efficient for case finding, but also accurate and precise enough for monitoring. In addition, the approach described herein provides resistance to optical blur and cataract, thereby helping to reduce the variability associated with the measurement of small changes in the visual field over time, which should strengthen the reliability of clinical evidence used for management decisions.

Electrophysiology experiments done in the 1970s show that all on-off ganglion cells show intracellular sensitivity to fine positional displacement (Scobey et al, 1981). The Moorfields MDT presents 32 vertically aligned stimuli which are orthogonally displaced, one at a time and by varying distances, to measure the sensitivity of the retina to displacement. As noted above, splitting the MDT displacements into red, green and blue sub-components in an attempt to use sub-pixellation has been found to cause psychophysical disadvantages, including the physiological variation of colour receptors with eccentricity and the different neural pathways concerned with colour processing. Furthermore, colour deficiencies may occur due to inherited photo-pigment abnormalities, the presence of cataract, and various ocular and neurological disease processes. A further disadvantage is that a distracting "rainbow" effect may be observed as an RGB sub-pixel is displaced.

The luminance of RGB computer displays is generally in a ratio of 1:2:1. However, the colour presentation may be somewhat variable across the field of view. RGB sub-pixel displacement thereby conflicts with the psychophysical properties of the motion displacement stimulus, where the threshold has been shown to be linearly related to the square root of the stimulus energy (area*luminance) relative to the background luminance (Verdon-Roe et al, 2006b).

One embodiment of the present invention therefore utilises a monochromatic (white-white-white) sub-pixel strategy for the MDT, in which each white sub-pixel is of equal energy (area*luminance). Such an approach therefore fulfils the requirements of the threshold energy displacement law specified above. In this embodiment, a monochromatic (www) 20-inch EIZO GS521 (dot pitch 0.165 mm) medical monitor was utilised because of its high quality build. The monitor is specifically designed for breast screening, and in this application is generally utilised in portrait mode. However, the monitor was rotated through 90 degrees to landscape orientation to encompass the configuration of the Moorfields MDT at 30 cm.

Figure 7:
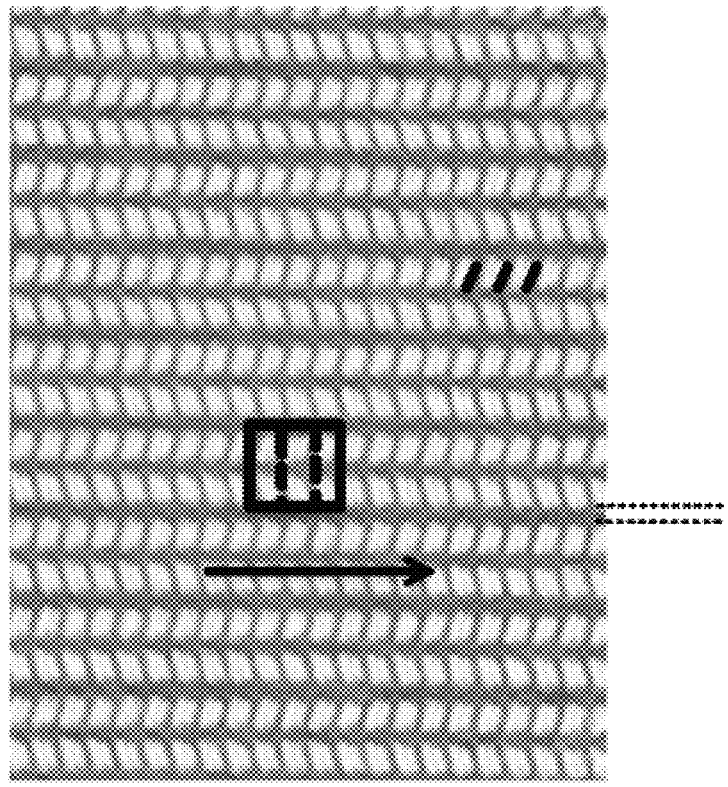
FIG. 7 is a photograph of a monitor having monochromatic sub-pixels in accordance with one embodiment of the invention.
Figure 7:
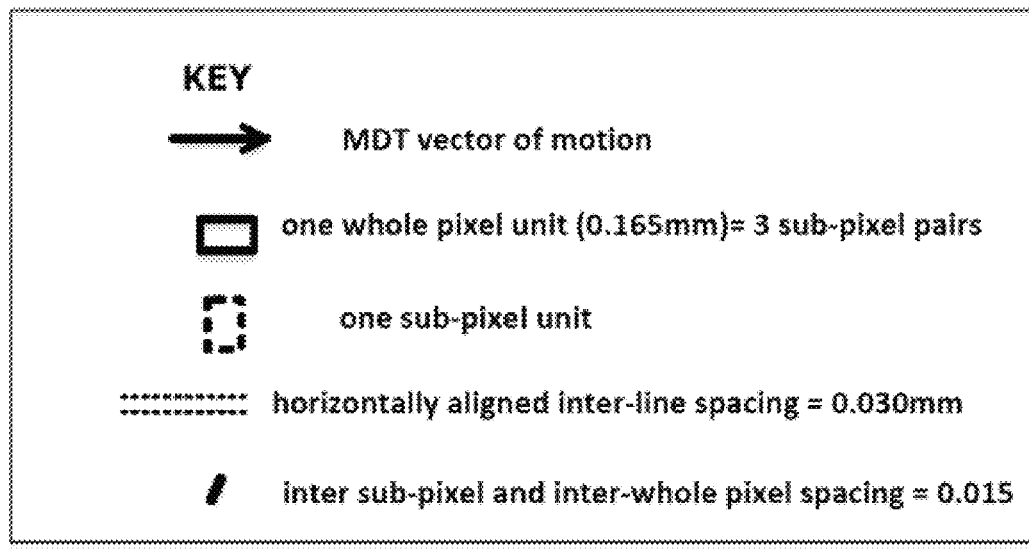

FIG. 7 presents a photograph of the sub-pixel configuration of the EIZO GS521 monochromatic monitor viewed through a Meade 26 mm telescope lens. The image has been magnified by approximately ×400. The inter-pixel, inter-sub-pixel and inter-line spacing dimensions are estimated by using the dot pitch (0.165 mm) as a reference. It can be seen from FIG. 7 that each pixel on the EIZO GS521 is composed of 3 sub-pixel pairs. The spacing between the sub-pixels in the horizontal direction matches the spacing between the pixels as a whole (in this direction).

It was confirmed that the stimulus dimensions are not altered through rotating the monitor (and, therefore, the line spacing between pixels) through 90 degrees. This was found not to be the case by measuring the on-screen stimulus dimensions and comparing them with the estimated size calculated from the pixel dot pitch. These findings are also supported by the observation that the orientation of the between line spacing of the EIZO GS521 monochromatic monitor in landscape mode (as shown in FIG. 7) corresponds to the between line spacing of (horizontally-mounted) rgb monitors used for previous MMDT studies.

In one embodiment, the MMDT stimulus configurations are stored as 24-bit bitmaps, in which each R/G/B element of a pixel is stored as an 8-bit value (giving a total of 256 possible values per colour). Given a row of 3 pixels (each composed of 3 sub-pixels) where 0 represents the sub-pixel 'off' and X represents the sub-pixel 'on' the following applies: OOO|XXX|OOO|. A shift to the left by one sub-pixel results in the following configuration: OOX|XXO|OOO. In low-level graphics memory terms this is equivalent to an 8-bit left arithmetic shift. Likewise, a two sub-pixels shift to the left is equivalent to a 16 bit left arithmetic shift: OXX|XOOO|OOO. The MMDT sub-pixel strategy exploits this principle. In particular, the MMDT sub-pixel strategy uses a function whereby a stimulus is taken and shifted N×8 bits, where N is an integer which represents the required sub-pixel displacement shift and may be positive or negative as appropriate. It will be appreciated that the above-mentioned 8-bit shifts are appropriate for a monitor with 24-bits and 3 sub-pixels per pixel—hence 8 bits per sub-pixel. Other monitors may have a different number of bits per sub-pixel, and hence will have a different shift (in bit terms) corresponding to a displacement of one sub-pixel.

The MMDT stimuli are moved towards the fixation spot. Accordingly, when testing the right eye, if the stimulus X-Axis position is <0, the stimulus will need to move to the right (+1 vector). Conversely, if the stimulus X-Axis position is >0, the stimulus will need to be moved to the left (−1 vector). The configuration of these vectors is mirror-flipped when testing the left eye.

Examples are provides below of one sub-pixel displacement of a bitmap image that is 8 pixels wide, with a stimulus bar of 3 pixels width, for the left and right eyes.

A Right Eye (i) Right eye: non-displaced starting position

```
 1  2   3    4    5   6  7  8
|---|---|WWW|WWW|WWW|---|---|---|
|---|---|WWW|WWW|WWW|---|---|---|
|---|---|WWW|WWW|WWW|---|---|---|
|---|---|WWW|WWW|WWW|---|---|---|
```

(ii) A displacement of one sub-pixel (0.33) with a vector of -1 toward the fixation point gives the following:

```
 1  2   3    4    5   6   7  8
|---|--W|WWW|WWW|WW-|---|---|---|
|---|--W|WWW|WWW|WW-|---|---|---|
|---|--W|WWW|WWW|WW-|---|---|---|
|---|--W|WWW|WWW|WW-|---|---|---|
```

B Left Eye (i) Left eye: non-displaced starting position

```
 1  2  3    4    5    6   7  8
|---|---|---|WWW|WWW|WWW|---|---|
|---|---|---|WWW|WWW|WWW|---|---|
|---|---|---|WWW|WWW|WWW|---|---|
|---|---|---|WWW|WWW|WWW|---|---|
```

(ii) Left eye: displacement of one sub-pixel (0.33) with a vector of +1 toward the fixation point

```
 1  2  3    4    5    6   7  8
|---|---|---|-WW|WWW|WWW|W--|---|
|---|---|---|-WW|WWW|WWW|W--|---|
|---|---|---|-WW|WWW|WWW|W--|---|
|---|---|---|-WW|WWW|WWW|W--|---|
```

Note that for left eye tests, the entire bitmap is mirror flipped, so that the starting position of the stimulus bar is shifted to the right by one pixel by comparison with the right eye (for stimuli that have a width corresponding to an odd number of pixels). Accordingly, an additional "whole pixel" shift is applied to the middle of the stimulus bar—i.e. the stimulus bar is located in columns (3)-(6) for the right eye, but columns (4)-(7) for the left eye. Note however that this shift only applies to stimuli that have a width comprising an odd number of pixels; for stimuli that that have an even number of pixels width, the additional pixel shift does not occur as the stimulus bar is mirrored perfectly along the vertical centre of the image.

In implementing the sub-pixel strategy, and an additional pair of bitmaps was generated for each stimulus location corresponding to the first and second sub-pixel displacement positions (i.e. by one and two sub-pixels respectively). An allowance was made for the mirror differences between the right and left eyes and also for differences between even and odd pixel width as discussed above.

Figure 8:
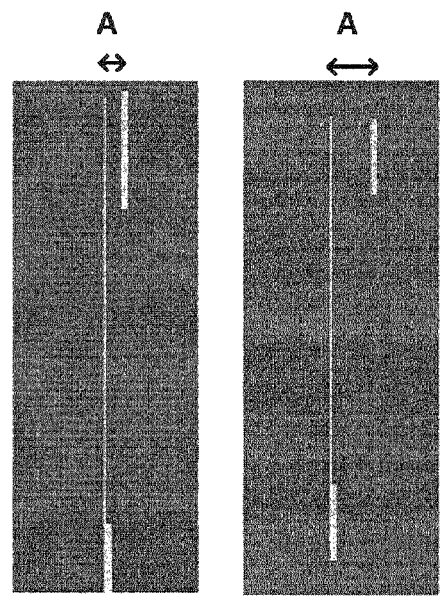
FIG. 8 illustrates a comparison of sub-pixel displacement against whole pixel displacement in accordance with one embodiment of the invention.

The accuracy of sub-pixel versus whole pixel displacements was verified using an automated test routine as follows: a) both the left and right eye tests at a sub-pixel level are flipped and stored; b) the flipped left eye results are compared with the right eye results, and likewise the flipped right eye results are compared with the left eye results; and c) base images are compared to the actual results relative to each eye, and a pass or fail displayed for each result. In addition, manual checks were performed by importing screenshots into a graphics program and viewing the screenshots with the pixel grid superimposed. The corresponding stimulus in the opposite hemifield was used as a reference for the starting position. One example of such a manual comparison is illustrated in FIG. 8, where the left image represents a subpixel displacement of 10 pixels, while the right image represents a corresponding whole pixel displacement of 30 pixels. In both cases, the displacement (as indicated by arrow (A)) is measured with respect to the thin vertical white line, whose (undisplaced) location is defined by the stimulus location shown at the bottom of the diagram. Note that in one embodiment, this test routine utilised the "Paint" program, which does not directly support sub-pixel viewing; nevertheless, the sub-pixel displacement could be determined by looking for colour fringing.

Various pilot studies were performed to compare the performance of the MMDT using the sub-pixel LCD displacement strategy, compared with the standard MMDT, in which the pixel size of conventional LCD monitors limits the resolution of the MMDT hyperacuity test to measure thresholds in areas of high retinal sensitivity. In these studies, the stimuli were presented on the high definition EIZO GS521 monitor mentioned above, which is a 20 inch LCD monochromatic monitor with a 0.165 mm pitch. Each pixel is composed of three white sub-pixels (or pairs of sub-pixels, as shown in FIG. 7), where each sub-pixel presents an equal "energy" (area * luminance).

Since it was found that the frame rate control (FRC) and the digital uniformity equalizer (DUE) settings of the EIZO software conflicted with the operation of the MMDT sub-pixel strategy, the FRC and DUE were disabled during the study. In addition, the field of uniformity of the EIZO monitor was measured and the monitor luminance values were adjusted to give the best estimate of equivalent luminance to the stimulus and background used for the collection of the MMDT normative database (stimulus luminance 102 $cd/m^2$, background luminance 9 $cd/m^2$).

Figure 9:
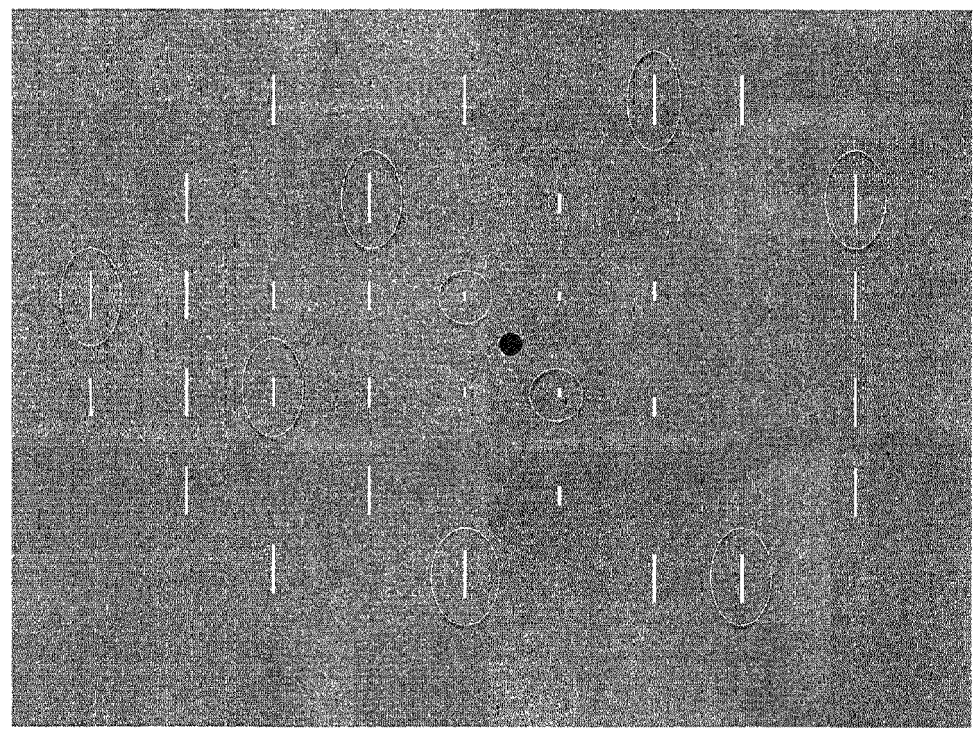
FIG. 9 illustrates the MMDT screen display for the right eye, and indicates the test locations utilised in the study of the sub-pixellation strategy in accordance with one embodiment of the invention.

The test was performed on 2 visually healthy subjects aged 28 and 30 years. People of this age generally have a high central density of retinal cells, and accordingly are sensitive to small displacements. The MMDT screen display for the right eye is shown in FIG. 9. Nine test locations were used (as indicated by the rings around the relevant vertical lines). The stimuli closer to the fixation spot (indicated approximately by the black dot in FIG. 9) are generally smaller (shorter vertical lines) than those stimuli further from the fixation spot (Garway-Heath et al 2000a). This reflects the higher density of retinal cells in the central portion of the field of view, which therefore increases sensitivity to a stimulus. The stimuli were scaled to a size appropriate to the oldest age band, 61+ years (Moosavi et al, 2008). It will be appreciated that as mentioned above, the oldest age band are generally presented with the largest stimuli (which means that such stimuli might conventionally be "all seen" by a younger person with a higher density of retinal cells).

The test was based on a multi-location frequency of seeing (FOS) program, in which there were 30 presentations for each step in displacement (for some of the studies). In particular, each test location was subject to increased displacement (for each step), and the proportion of times at which the stimulus was viewed for this step was determined. For each presentation, there are generally 3 oscillations of the vertical line, at 200 ms per cycle. The (valid) response time for each presentation was set at 1500 ms (in addition to the 600 ms presentation time).

Figure 10:
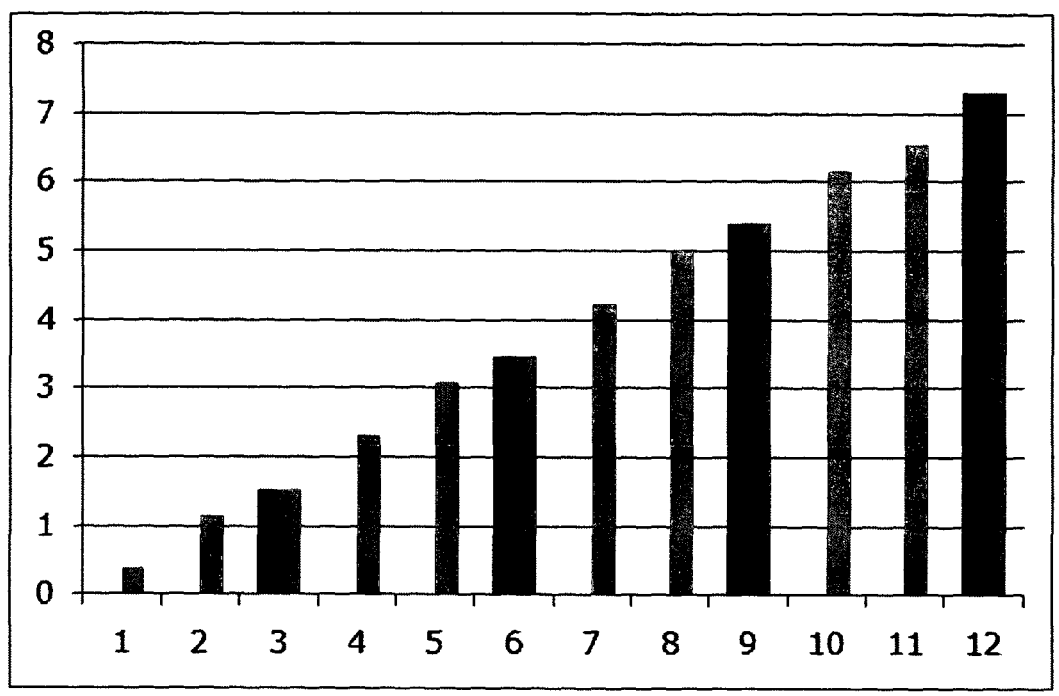
FIG. 10 is a schematic illustration that compares the incremental displacements used for the whole pixel testing and the sub-pixel testing in accordance with one embodiment of the invention.

FIG. 10 illustrates in schematic form the displacement increments used for the sub-pixel test (red) and the whole pixel test (blue) (the x-axis is in units of the sub-pixel spacing interval). The use of the sub-pixel strategy increases the number of incremental steps by a factor of 3, since the sub-pixel strategy allows the displacement to be incremented by a third of the inter-(whole)pixel spacing. For example, in this study, the first sub-pixel step occurs at 0 minutes and 37 seconds of arc (00:37), whereas the first whole pixel step occurs at 1 minute and 52 seconds of arc (01:52), corresponding to three sub-pixel displacements. This pattern then repeats, in that a whole pixel displacement is available at every third sub-pixel displacement.

Table 1 below lists the full set of displacements presented in one study to the subjects at each of the various test locations. (Note that because of symmetry, the first column of data in Table 1, corresponding to location −03, +03, also applies to locations −03, −03; +03, −03 and 03, +03). The data of Table 1 can therefore be considered as corresponding generally to FIG. 10). In particular, the rows marked as WP=1, 2, etc, correspond to whole pixel displacements. The displacements are specified in arc minutes (and arc seconds). The angular displacement for a whole pixel (or sub-pixel) shift depends on the dot pitch of the monitor and the position of the stimulus. The EIZO GS521 monitor has a relatively small dot pitch (=high definition) of 0.165 mm, which is considerably lower than the standard dot pitch of many conventional monitors (typically about 0.255 mm). The lower dot pitch of the EIZO GS521 monitor results in a lower angular displacement per pixel, and hence increased granularity of resolution.

The position of the stimulus impacts the angular displacement per pixel for geometric reasons. In particular, if we define a central axis from the eye to the central fixation point, then for off-axis stimuli, the angular displacement per pixel decreases with distance from the central fixation point, since the distance from the eye to the stimulus is greater, and also the plane of the monitor is no longer perpendicular to the line of sight—i.e. there is a foreshortening effect As can be seen from Table 1, the maximum size of the displacement for the stimuli provided to the subject increases away from the fixation point (centre of vision). This is because of the lower sensitivity of these peripheral regions. Note that in the study, the displacements were randomly presented and divided into short sessions of acceptable duration to prevent subject fatigue.

TABLE 1

| Sub-Pixel Displacement | Frequency of Seeing Test Locations | | | | | | | |
|---|---|---|---|---|---|---|---|---|
| | −03, +03 | −09, +09 | +09, +15 | −03, −15 | −15, −03 | 15, −15 | + 21, +09 | −27, +03 |
| 1 | 00:37 | 00:36 | 00:35 | 00:36 | 00:35 | 00:34 | 00:32 | 00:29 |
| 2 | 01:15 | 01:12 | 01:11 | 01:12 | 01:10 | 01:08 | 01:05 | 00:59 |
| 3 (WP = 1) | 01:52 | 01:49 | 01:46 | 01:49 | 01:45 | 01:42 | 01:37 | 01:29 |
| 4 | 02:30 | 02:55 | 02:22 | 02:25 | 02:20 | 02:16 | 02:10 | 01:59 |
| 5 | 03:08 | 03:02 | 02:58 | 03:02 | 02:56 | 02:51 | 02:43 | 02:29 |
| 6 (WP = 2) | 03:45 | 03:38 | 03:33 | 03:38 | 03:31 | 03:25 | 03:15 | 02:59 |
| 7 | 04:23 | 04:15 | 04:09 | 04:14 | 04:06 | 03:59 | 03:48 | 03:29 |
| 8 | 05:01 | 04:51 | 04:45 | 04:51 | 04:41 | 04:33 | 04:21 | 03:59 |
| 9 (WP = 3) | 05:38 | 05:27 | 05:21 | 05:27 | 05:16 | 05:07 | 04:53 | 04:29 |
| 10 | 06:16 | 06:04 | 05:56 | 06:04 | 05:52 | 05:42 | 05:26 | 04:59 |
| 11 | 06:53 | 06:40 | 06:32 | 06:40 | 06:27 | 06:16 | 05:59 | 05:29 |
| 12 (WP = 4) | 07:31 | 07:17 | 07:08 | 07:16 | 07:02 | 06:50 | 06:31 | 05:59 |
| 13 | | | | 07:53 | 07:37 | 07:24 | | 06:30 |
| 14 | | | | 08:29 | 08:13 | 07:59 | | 07:00 |
| 15 (WP = 5) | | | | 09:06 | 08:48 | 08:33 | | 07:30 |
| 16 | | | | | | | | 08:00 |
| 17 | | | | | | | | 08:30 |
| 18 (WP = 6) | | | | | | | | 09:00 |
| 19 | | | | | | | | 09:30 |
| 20 | | | | | | | | 10:00 |
| 21 (WP = 7) | | | | | | | | 10:30 |

The four central stimuli used for the collection of the MMDT normative database were not scaled by estimates of RGC density because the stimuli were adjusted in size to be resistant to the effects of refractive blur. This has advantages for case-detection in the community, where facilities to measure optical correction and use wide aperture lenses may not be available. However, it is helpful to scale the central stimulus size and test with optical correction for the purposes of monitoring for glaucoma in the hospital or specialist optometry setting. Bitmaps were therefore also created to provide a smaller scaled stimulus size for the 4 locations located within three degrees of central fixation. The new central stimulus area was approximately 50% of the central stimulus area used for the normative database tests, corresponding to previously calculated scaling estimates (see Garway-Heath, 2000a, and Verdon-Roe, 2006a).

Figure 11:
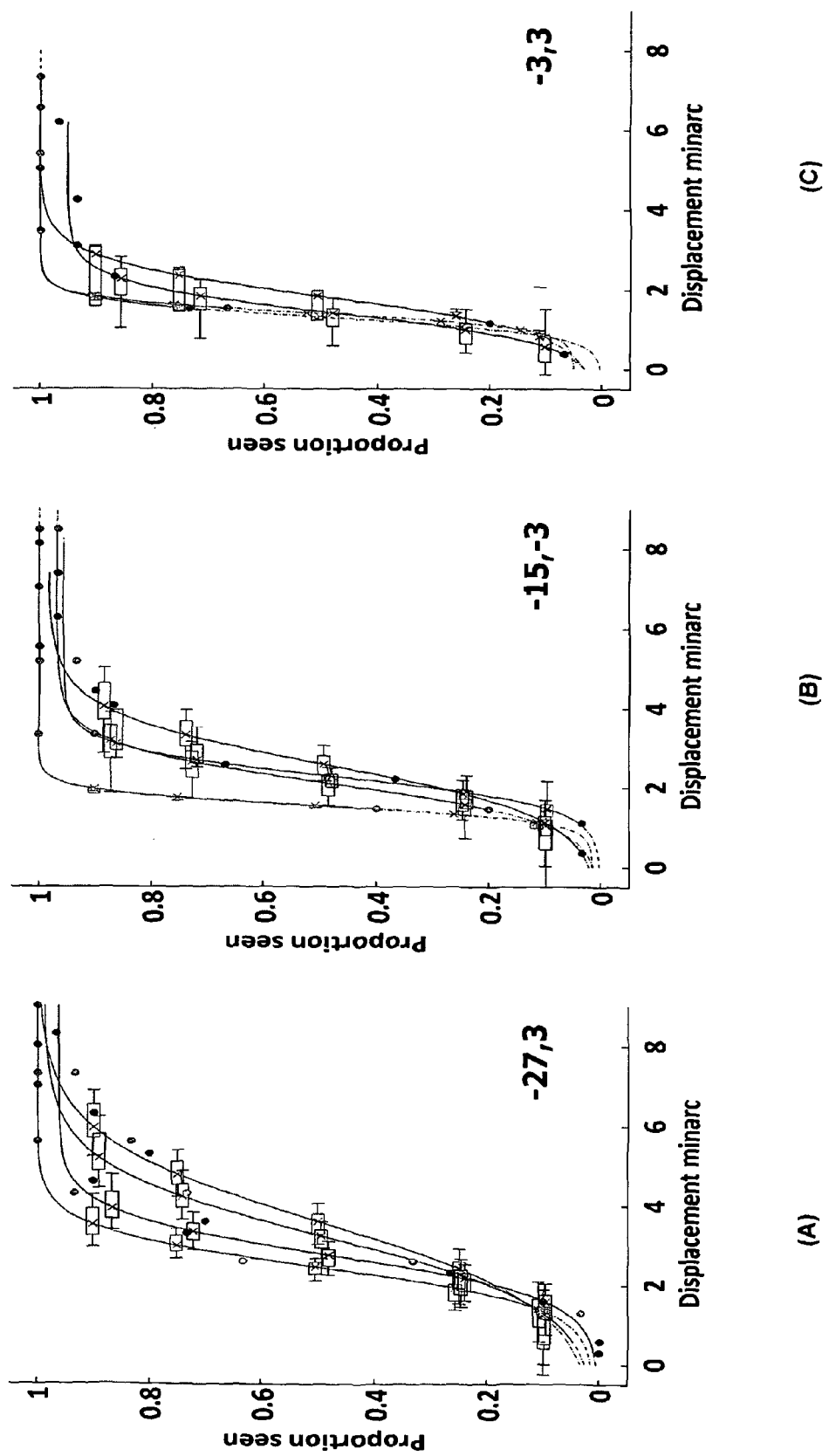
FIGS. 11, 12 and 13 present plots of frequency of seeing (FOS) against displacement for various retinal test locations, including results from studies of a sub-pixel testing strategy in accordance with various embodiments of the invention.
Figure 12:
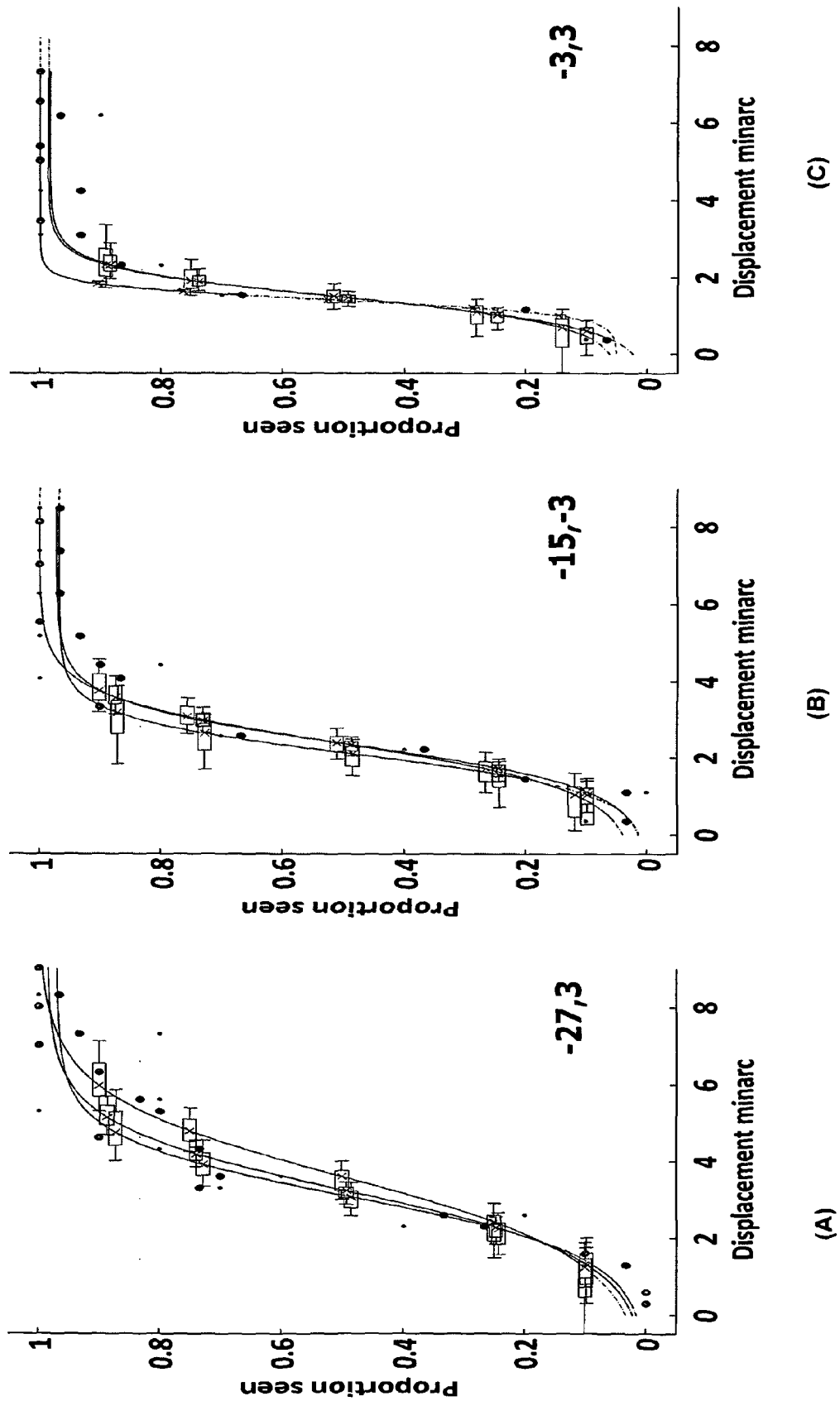

The results from the studies were analysed using a maximum-likelihood method as described in Wichman and Hill, 2001 to determine 50% seen thresholds, 95% confidence intervals (CIs) and slopes). The results from some of the studies are shown in FIGS. 11 and 12. Each of FIGS. 11 and 12 depicts the proportion of presentations seen against displacement (in arc minutes). The three plots in each Figure denoted (A), (B) and (C) correspond to three different test locations within the field of view, namely (−27, 3), (−15, −3), and (−3, 3) respectively (the numbers correspond to position co-ordinates in FIG. 9, where the black dot indicates the zero point or origin). Note that the three test locations of FIGS. 11 and 12 become progressively closer to the centre of the field of view, and therefore correspond to regions of increasing sensitivity. This is generally reflected in the plots, in which the curves become steeper towards the right of the diagram (i.e. plot (C) has a steeper curve than plot (A)). In particular, the proportion of presentations seen reaches close to unity at a lower displacement for plot (C) at location (−3, 3) than for plot (A) at location (−27, 3) (with plot (B) at location (−15, −3) having an intermediate result).

Each plot in FIG. 11 shows four lines. One line (light blue) corresponds to the results from the whole pixel strategy. The remaining three lines derive from the sub-pixellation strategy. In particular, the lines are taken from whole pixel intervals, but with different starting positions, so that the dark blue line corresponds to pixel positions 0.33, 1.33, 2.33 . . . etc, the green line corresponds to pixel positions 0.66, 1.66, 2.66 . . . etc, and the red line corresponds to pixel positions 1.0, 2.0, 3.0 . . . etc. Confidence intervals are shown with respect to the 10%, 25%, 50%, 75% and 90% levels of seeing the presentation. Note that confidence intervals were not measurable in FIG. 11 for whole pixel displacements at (−3, 3), but were measurable when using the sub-pixel strategy.

Each plot in FIG. 12 shows 3 lines. The blue line represents the FOS curve for a reference standard, while the green line represents the FOS curve based on the whole pixel measurements (30 presentations per position). The red line is derived from the sub-pixellation data, in particular the first 10 presentations for each displacement (which then corresponds to the same overall number of presentations as for the whole pixel strategy, so as to remove any effect of sampling bias). Again, confidence intervals (where measurable) are shown with respect to the 10%, 25%, 50%, 75% and 90% levels of seeing the presentation. The sub-pixel sampling generally shows tighter confidence intervals than were obtained from the whole pixel strategy. Also, certain confidence intervals could not be obtained for some locations using a whole pixel strategy, but were obtained using the sub-pixellation strategy.

Figure 13:
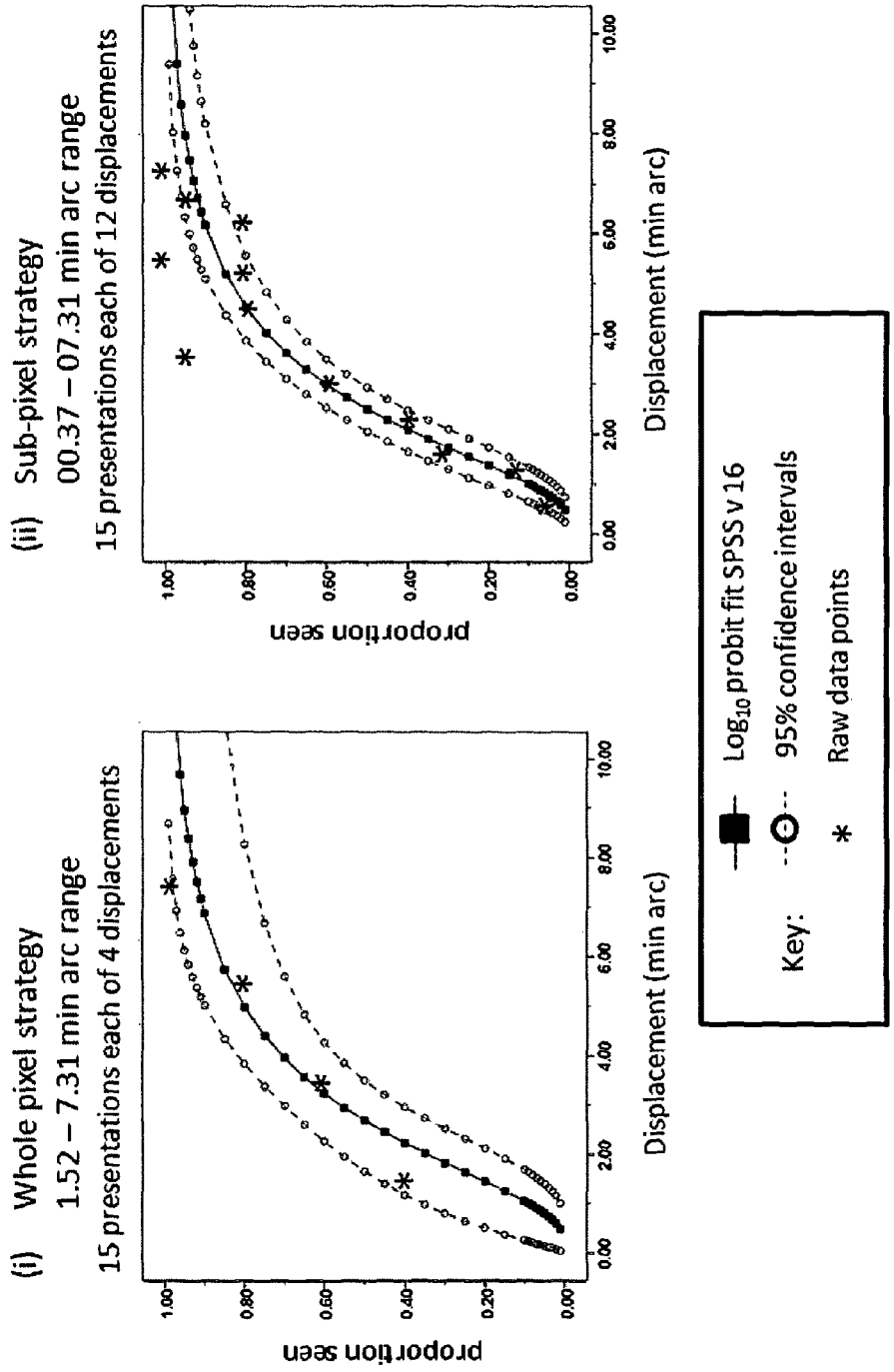

FIG. 13 illustrates some results of another study in which the MMDT 32-location test was presented on an EIZO GS521 monochromatic monitor (0.165 mm pitch). The right eye of two healthy subjects (aged 25 and 20 years) was tested. Frequency of seeing (FOS) curves were generated at the 9 locations shown in FIG. 9 for whole and sub-pixel motion displacements using a multi-location FOS test strategy. 15 presentations were made for each increment of displacement. FOS curves were generated and 95% confidence intervals (CI) compared between the two strategies (Wilcoxon test; SPSS version 16; $\log_{10}$ probit fit). As can be seen from FIG. 13, which illustrates the FOS results for one subject at one central location, the sub-pixel strategy extended the lower end of the MMDT dynamic test range for locations where responses at the smallest whole pixel displacement were seen. The finer increments of displacement provided by the sub-pixel strategy significantly narrowed the CIs (P<0.01). The mean reduction for the 95% CI at the 50% threshold for the two central locations was 23% (although this does not allow for sampling effects, given the greater number of presentations used for the sub-pixel strategy compared with the whole pixel strategy.

In one embodiment, the sub-pixel strategy may be used to help separate ESTA cut-offs at different percentage levels (e.g. 92%, 95% and 98%) where the differences between these cut-offs are very small and, when converted from arc minute values, may give the same whole pixel figures (i.e. the differences may be lost in the quantization to whole pixels. In such a situation, the use of the sub-pixel strategy can provide better definition of the relevant threshold levels.

As an example, Table 2 below gives estimates of cut-off values in minutes of arc for the central location (3, 3) of the MMDT. It can be seen that the differences between some of these values for different cut-off values are smaller than the whole pixel displacement values (typically 1.3-1.5 minutes of arc) specified in Table 1.

TABLE 2

| Age | 92% | 95% | 98% |
| --- | --- | --- | --- |
| 20 | 6.983646 | 7.595475 | 9.606276 |
| 21 | 7.022642 | 7.63447 | 9.645271 |
| 22 | 7.061637 | 7.673466 | 9.684267 |
| 23 | 7.100633 | 7.712462 | 9.723263 |
| 24 | 7.139629 | 7.751458 | 9.762259 |
| 25 | 7.178625 | 7.790453 | 9.801254 |

Overall, the MMDT sub-pixel LCD strategy provides a three-fold increase in resolution for displacements, and therefore helps to extend the high sensitivity (low displacement) end of the dynamic test range and to improve measurement precision. The greater dynamic range and precision of the sub-pixel measurements can help to improve threshold estimation, and also support the application of the MMDT for monitoring for glaucoma progression.

Although various embodiments of the invention are described above, the skilled person will be aware of many modifications and variations on these embodiments that will remain within the scope of the present invention, which is therefore defined by the appended claims and their equivalents.

REFERENCES

Anderson, R. S., M. O. Wilkinson, et al. (1992). Psychophysical localization of the human visual streak. *Optom Vis Sci.* 69 (3): 171-4.

Fitzke FW, Poinoosawmy D, Ernst W, Hitchings RA. Peripheral displacement thresholds in normals, ocular hypertensives and glaucoma., in *Perimetry Update* 1986/1987, E. Greve and A. Heijl, Editors, Kugler & Ghedini: The Hague, The Netherlands. 447-452.

Garway-Heath, D. F., J. Caprioli, et al. Scaling the hill of vision: the physiological relationship between light sensitivity and ganglion cell numbers. *Invest Ophthalmol Vis Sci.* 2000a. 41 (7): 1774-82.

Garway-Heath DF, Poinoosawmy D, Fitzke FW.Hitchings RA. Mapping the visual field to the optic disc in normal tension glaucoma eyes. *Ophthalmology.* 2000b;107(10): 1809-15.

Georgeson MA, Freeman TCA, Scott-Samuel NE, Sub-pixel Accuracy: Psychophysical Validation of an Algorithm for Fine Positioning and Movement of Dots on Visual Displays. *Vision Res.* 1996 36(4): 605-612.

Hock, H. S., G. W. Balz, et al. (1998). Attentional control of spatial scale: effects on self-organized motion patterns. *Vision Res.* 38 (23): 3743-58.

Moosavi R, Verdon-Roe GM, Westcott MC, Crabb DP, Viswanathan AC, Fitzke FW, Garway-Heath DF. Comparison of the effect on Moorfields Motion Test (MDT) thresholds of stimulus scaling for eccentricity and age. *Invest Ophthalmol Vis Sci.* 2008: ARVO E-Abstract 1083.

Scobey RP, Johnson CA. Psychophysical properties of displacement thresholds for moving targets. *Acta Psychol (Amst)*. 1981;48:49-55.

Strouthidis NG, Vinciotti V, Tucker AJ, Gardiner SK, Crabb DP and Garway-Heath DF. Structure and Function in Glaucoma: The Relationship between a Functional Visual Field Map and an Anatomic Retinal Map. *Invest Ophthalmol Vis Sci.* 2006 47: 5356-5362.

Verdon-Roe GM, Westcott MC, Viswanathan AC, Fitzke F W, Hitchings RA. Optimum number of stimulus oscillations for motion displacement detection in glaucoma, in *Perimetry Update* 2000/2001, M. Wall and J. Wild, Editors, Kugler Publications: The Hague, The Netherlands pp 97-102.

Verdon-Roe GM, Development of a multi-location motion displacement test for detection of early glaucoma. Doctoral Thesis (2006a) *Institute of Ophthalmology, University College London*.

Verdon-Roe GM, Westcott MC, Viswanathan AC, Fitzke FW.Garway-Heath DF. Exploration of the psychophysics of a motion displacement hyperacuity stimulus. *Invest Ophthalmol Vis Sci.* 2006b. 47(11):4847-55.

Viswanathan AC. Loading a CBitmap Object from a BMP File. *Windows Developers Journal,* 2000. 11(10): 68.

Verdon-Roe, GM, Westcott MC, Moosavi R, Gore D, Viswanathan AC, Garway-Heath DF. (2006c). The effect of stimulus orientation, learning and central refraction on a new multilocation motion displacement test for the detection of glaucoma. *International Perimetric Society Meeting, Portland, Oregon.* Paper presentation.

Westcott MC, Verdon-Roe GM, Viswanathan AC, Fitzke FW, Hitchings RA. Optimum stimulus duration for motion displacement detection in glaucoma, in *Perimetry Update* 2000/2001, M. Wall and J. Wild, Editors, Kugler Publications: The Hague, The Netherlands pp 103-108.

Wichmann FA, Hill NJ. Percept Psychophys 2001; 63:1293-1313

The invention claimed is:

1. Apparatus for performing a supra-threshold test at a set of multiple locations spread across a visual field of a subject, said apparatus comprising:
 a processor;
 a memory; and
 a display mechanism;
 said apparatus being configured to:
  for each given location in the set of locations, define a cluster of multiple locations in the set of locations which are associated with said given location according to respective correlations between said given location and other locations in the set of locations, wherein the cluster is defined based on paths of optic nerve fibre bundles across the visual field;
  present a stimulus at each location in the set of locations and obtain a respective result for each location indicating whether or not the stimulus was seen by the subject at that location;
  estimate, for each given location in the set of locations, a probability of true damage (PTD) based on combining the results obtained from the multiple locations of the cluster associated with said given location;
  determine, for each given location in the set of locations, whether the probability of true damage is between an upper threshold T1 and a lower threshold T2, such that T1>PTD>T2, and if so, select said given location for presentation of a further stimulus;
  present a further stimulus at each selected given location in accordance with said determination and update the estimated PTD for the each selected given location; and
  output a binary map indicating a pass or fail at each of said set of locations as a result of the supra-threshold test, wherein a given location is marked as failed if PTD>T1.

2. The apparatus of claim 1, wherein the apparatus is further configured to provide a weights array corresponding to said cluster, whereby each location in the cluster is allocated a weight, and said combining comprises filtering the results using said weights array.

3. The apparatus of claim 2, wherein the apparatus is further configured to perform an examination of the filtered results to determine whether or not to re-present a stimulus at a given location.

4. The apparatus of claim 1, wherein the apparatus is further configured to adjust stimulus intensity prior to performing a re-presentation of the stimulus.

5. The apparatus of claim 1, wherein the apparatus is further configured to perform multiple cycles of said presenting, obtaining and determining.

6. The apparatus of claim 5, wherein the apparatus is configured to terminate said cycles if it is determined not to re-present the stimulus at any location, or if a predetermined maximum number of cycles have been performed.

7. The apparatus of claim 1, wherein the correlation between the primary location and a secondary location is calculated using a parameter based on the paths of optic nerve fibre bundles across the visual field that pass through or close to the primary location and the secondary location.

8. The apparatus of claim 7, wherein said parameter is based on the angle between (i) a first optic nerve fibre bundle that passes through the primary location; and (ii) a second optic nerve fibre bundle that passes through the primary location.

9. The apparatus of claim 8, wherein said angle between the first optic nerve fibre bundle and the second optic nerve fibre bundle is measured at the optic nerve head.

10. The apparatus of claim 1, wherein the correlation is further based on the retinal distance between the primary location and the secondary location.

11. The apparatus of claim 1, wherein the apparatus is configured to add a secondary location to the cluster for the primary location if the correlation between the primary location and the secondary location exceeds a predetermined threshold.

12. The apparatus of claim 1, wherein the apparatus is further configured to determine a weight for each secondary location in the cluster based on the correlation between that secondary location and the primary location.

13. A method for performing a supra-threshold test at a set of multiple locations spread across a visual field of a subject, said method comprising:

for each given location in the set of locations, defining a cluster of multiple locations in the set of locations which are associated with said given location according to respective correlations between said given location and other locations in the set of locations, wherein the cluster is defined based on paths of optic nerve fibre bundles across the visual field;

presenting, by a computer, a stimulus at each location in the set of locations and obtaining, by the computer, a respective result for each location indicating whether or not the stimulus was seen by the subject at that location;

estimating, by the computer, for each given location in the set of locations, a probability of true damage (PTD) based on combining the results obtained from the multiple locations of the cluster associated with said given location;

determining, for each given location in the set of locations, whether the probability of true damage is between an upper threshold T1 and a lower threshold T2, such that T1>PTD>T2, and if so, select said given location for presentation of a further stimulus;

presenting a further stimulus at each selected given location in accordance with said determination and updating the estimated PTD for the each selected given location; and outputting a binary map indicating a pass or fail at each of said set of locations as a result of the supra-threshold test, wherein a given location is marked as failed if PTD>T1.

14. A non-transitory computer program product comprising program instructions that when executed by a computer cause the computer to perform a supra-threshold test at a set of multiple locations spread across a visual field of a subject comprising:

for each given location in the set of locations, defining a cluster of multiple locations in the set of locations which are associated with said given location according to respective correlations between said given location and other locations in the set of locations, wherein the cluster is defined based on paths of optic nerve fibre bundles across the visual field;

presenting, by the computer, a stimulus at each location in the set of locations and obtaining, by the computer, a respective result for each location indicating whether or not the stimulus was seen by the subject at that location;

estimating, by the computer, for each given location in the set of locations, a probability of true damage (PTD) based on combining the results obtained from the multiple locations of the cluster associated with said given location;

determining, for each given location in the set of locations, whether the probability of true damage is between an upper threshold T1 and a lower threshold T2, such that T1>PTD>T2, and if so, select said given location for presentation of a further stimulus;

presenting a further stimulus at each selected given location in accordance with said determination and updating the estimated PTD for the each selected given location; and outputting a binary map indicating a pass or fail at each of said set of locations as a result of the supra-threshold test, wherein a given location is marked as failed if PTD>T1.

* * * * *